US007482004B2

(12) United States Patent
Carmeliet et al.

(10) Patent No.: US 7,482,004 B2
(45) Date of Patent: Jan. 27, 2009

(54) INHIBITORS OF PLACENTAL GROWTH FACTOR FOR THE TREATMENT OF PATHOLOGICAL ANGIOGENESIS, PATHOLOGICAL ARTERIOGENESIS, INFLAMMATION, TUMOR FORMATION AND/OR VASCULAR LEAKAGE

(75) Inventors: Peter Carmeliet, Landen (BE); Désiré Collen, Winksele (BE); Sandro De Falco, Naples (IT); Ruvo Menotti, Tervico (IT)

(73) Assignees: Vlaams Interuniversitair Instituut voor Biotechnologie vzw, Zwijnaarde (BE); Life Sciences Research Partners vzw., Leuven (BE)

( * ) Notice: Subject to any disclaimer, the term of this patent is extended or adjusted under 35 U.S.C. 154(b) by 315 days.

(21) Appl. No.: 10/291,979

(22) Filed: Nov. 11, 2002

(65) Prior Publication Data

US 2003/0180286 A1  Sep. 25, 2003

Related U.S. Application Data

(63) Continuation of application No. PCT/EP01/05478, filed on May 10, 2001.

(30) Foreign Application Priority Data

May 12, 2000  (EP) .................................. 00201714

(51) Int. Cl.
*A61K 39/395* (2006.01)
(52) U.S. Cl. ................................ 424/145.1; 424/145.1
(58) Field of Classification Search .............. 424/130.1, 424/145.1
See application file for complete search history.

(56) References Cited

U.S. PATENT DOCUMENTS

| 5,545,806 A | 8/1996 | Lonberg et al. |
| 5,851,999 A | 12/1998 | Ullrich et al. |

FOREIGN PATENT DOCUMENTS

| WO | WO 84/03564 | 9/1984 |
| WO | WO 9924056 A1 * | 5/1999 |
| WO | WO 99/60846 | 12/1999 |

OTHER PUBLICATIONS

Miller (Breast Cancer Treatment and Research, 2002, 75: S45-S50).*
MSNBC News Services, "Mixed results on new cancer drug", Nov. 9, 2000.*
Gura (Science, vol. 278, 1997, pp. 1041-1042).*
Colucciello (Postgraduate Medicine online, 2004, vol. 116, No. 1 (Proliferative Diabetic Retinopathy) available at http://www.postgradmed.com/issues/2004/07_04/colucciello.htm.*
Johnstone and Thorpe (Immunochemistry in Practice, Blackwell Scientific Publications, Oxford, 1987, pp. 30).*
Kohler and Milstein (Nature 1975, 256:495-497), reprinted in the Journal of Immunology pp. 2453-2455.*
Queen et al (PNAS, 1989, 86:10029-10033).*
Donnini et al (J. Pathol., 1999, 189 :66-71).*
PCT International Search Report, PCT/EP01/05478, dated Nov. 20, 2001.
Barillari et al., "The Basic Residues of Placenta Growth Factor Type 2 Retrieve Sequestered Angiogenic Factors into a Soluable Form: Implications for Tumor Angiogenesis," American Journal of Pathology, May 1998, pp. 1161-1166, vol. 152, No. 5.
Ziche et al., "Placenta Growth Factor-1 is Chemotactic, Mitogenic, and Andiogenic," Laboratory Investigation, 1997, pp. 517-531. vol. 76, No. 4.
Bottomley et al., "Placental growth factor (PlGF) induces vascular endothial growth factor (VEGF) secretion from mononuclear cells and is co-expressed with VEGF in synovial fluid," Clin Exp Immunol, 2000, pp. 182-188, vol. 119.
Park et al., "Placenta Growth Factor: Potentiation of Vascular Endothelial Growth Factor Bioactivity, in vitro and in vivo, and High Affinity Binding to Flt-1 but not to Flk-1/KDR," The Journal of Biological Chemistry, Oct. 14, 1994, pp. 25646-25654, vol. 269, No. 41.
Yonekura et al., "Placental Growth Factor and Vascular Endothelial Growth Factor B and C Expression in Microvascular Endothelial Cells and Pericytes," The Journal of Biological Chemistry, Dec. 3, 1999, pp. 35172-35178, vol. 247, No. 49.
Midgal et al., "Neuropilin-1 Is a Placenta Growth Factor-2 Receptor," The Journal of Biological Chemistry, Aug. 28, 1998, pp. 22272-22278, vol. 273, No. 35.
Research and Development Systems, Inc., "Monoclonal Anti-mouse PlGF-2 Antibody," Oct. 18, 1999, Catalog No. MAB465.
Research and Development Systems, Inc., "Biotinylated Anti-mouse PlGF-2 Antibody," Jan. 21, 1999, Catalog No. BAF465.
Hansma et al., Recombinant human endostatin administered as a 28-day continuous intravenous infusion, followed by daily subcutaneous injections: a phase I and pharmacokinetic study in patients with advanced cancer, Annals of Oncology, 2005, pp. 1695-1701, vol. 16.
Declerck et al., Generation of Monoclonal Antibodies against Autologous Proteins in Gene-inactivated Mice, The Journal of Biological Chemistry, 1995, pp. 8397-8400, vol. 270, No. 15.

(Continued)

*Primary Examiner*—Brandon J Fetterolf
(74) *Attorney, Agent, or Firm*—TraskBritt (57) ABSTRACT

The present invention relates to the field of pathological angiogenesis and arteriogenesis and, in particular, to a stress-induced phenotype in a transgenic mouse (PlGF$^{-/-}$) that does not produce Placental Growth Factor (PlGF) and that demonstrates an impaired vascular endothelial growth factor (VEGF)-dependent response. PlGF deficiency has a negative influence on diverse pathological processes of angiogenesis, arteriogenesis and vascular leakage comprising ischemic retinopathy, tumor formation, pulmonary hypertension, vascular leakage (edema formation) and inflammatory disorders. The invention thus relates to molecules that can inhibit the binding of PlGF to its receptor (VEGFR-1), such as monoclonal antibodies and tetrameric peptides, and to the use of these molecules to treat the above-mentioned pathological processes.

9 Claims, 1 Drawing Sheet

OTHER PUBLICATIONS

Submissions of applicant in the response to the summons for oral proceedings of the corresponding European patent application EP-A1-1 297 016 (01943357.2).
RYAN et al., 1999, Toxicol. pathol. 27, 78-86.
Takahashi et al., 1994, Cancer Res. 54, 4233-4237.
Viglietto et al., 1995, Oncogene, 11, 1569-1579.
Viglietto et al., 1996, Oncogene, 13, 577-587.
Weindel et al., 1994, Neurosurgery 35, 439-449.
Guidi, A.J. et al., 1996, Cancer 78, 454-460.
Hazelton et al., 1999, Curr. Oncol. Rep. 1, 59-63.
Katoh, R. et al., 1999, Human Pathol. 30, 891-897.
Nicol, D. et al., 1997, J. Urol. 157, 1482-1486.
Maglione et al., 1993, Oncogene 8, 925-931.
Paleolog et al., 1998, Angiogenesis 2, 295-307.
Oliver et al., 1995, Cell Immunol. 166, 196-206.
Fiddler Cancer angiogenesis in 'Cancer, Principles and Practice of Oncology' 6th Edition, Lippincott Williams & Wilkins eds.
Griffioen & Molema, 2000, Pharmacology Reviews, 52, 237-268.
Grounds of the Opposition against the corresponding European patent EP-B1-1 297 016 (01943357.2).

Additional documents cited in Grounds of the Opposition against the corresponding European patent application EP-A1-1 297 016 (01943357.2).
Folkman, 1995, N. Engl. J. Med. 333, 1757-1763.
Bicknell, 1997, in Tumor Angiogenesis, Chapter 2, pp. 1-3, 5-18.
Maragoudakis, 2000, in Proceedings Biann. Int. Meeting Angiogenesis, Jul. 1999, Introduction p. 1-4.
Carmeliet, 2000, Nature Med. 6, 389-395.
Nomura, 1998, J. Neuro-oncol, 40, 123-130.
Fischer et al., Anti-PlGF Inhibits Growth of VEGF(R)-Inhibitor-Resistant Tumors without Affecting Healthy Vessels, Cell, Nov. 2, 2007, pp. 463-475, vol. 131.
Jain et al., alpha-PlGF: A New Kid on the Antiangiogenesis Block, Cell, Nov. 2, 2007, pp. 443-445, Vol. 131.
Christinger et al., The Crystal Structure of Placental Growth Factor in Complex with Domain 2 of Vascular Endothelial Growth Factor Receptor-1, The Journal of Biological Chemistry, Mar. 12, 2004, pp. 10382-10388, vol. 279, No. 11.
Paques et al., Growth Factors and Diabetic Retinopathy, Diabetes & Metabolism, 1997, pp. 125-130, vol. 23.

* cited by examiner

Figure 1

INHIBITORS OF PLACENTAL GROWTH FACTOR FOR THE TREATMENT OF PATHOLOGICAL ANGIOGENESIS, PATHOLOGICAL ARTERIOGENESIS, INFLAMMATION, TUMOR FORMATION AND/OR VASCULAR LEAKAGE

CROSS-REFERENCE TO RELATED APPLICATION

This application is a continuation of PCT International application no. PCT/EP01/05478 filed May 10, 2001, designating the United States of America, published as WO 01/85796 A2 in the English language on Nov. 15, 2001, the contents of which is incorporated herein by this reference.

FIELD OF THE INVENTION

The invention relates to the field of pathological angiogenesis and arteriogenesis. In particular, the invention describes a stress-induced phenotype in a transgenic mouse (PlGF−) that does not produce Placental Growth Factor (PlGF) and that demonstrates an impaired vascular endothelial growth factor (VEGF)-dependent response. It is revealed that PlGF deficiency has a negative influence on diverse pathological processes of angiogenesis, arteriogenesis and vascular leakage comprising ischemic retinopathy, tumor formation, pulmonary hypertension, vascular leakage (edema formation) and inflammatory disorders. The invention thus relates to molecules that can inhibit the binding of PlGF to its receptor (VEGFR-1), such as monoclonal antibodies and tetrameric peptides. The invention further relates to the use of these molecules to treat the above-mentioned pathological processes.

BACKGROUND OF THE INVENTION

Abnormal blood vessel formation contributes to the pathogenesis of numerous diseases with high morbidity and mortality. Elucidation of the mechanisms underlying vascular growth might allow the development of therapeutic strategies to stimulate vascular growth in ischemic tissues or to suppress their formation in tumors. Recent gene targeting studies in embryos have identified some of the mechanisms involved in the initial formation of endothelial channels (angiogenesis) and their subsequent maturation by coverage with smooth muscle cells (arteriogenesis). Evidence is emerging that distinct molecular mechanisms may mediate growth of blood vessels during pathological conditions, but the molecular players remain largely undetermined.

VEGF has been implicated in development and pathological growth of the vasculature (N. Ferrara et al., 1999, Curr. Top. Microbiol. Immunol. 237, 1-30). Deficiency of a single VEGF allele causes fatal vascular defects (P. Carmeliet et al., 1996, Nature 380, 435-439; and N. Ferrara et al., 1996, Nature 380, 439-442), whereas suppression of VEGF in the neonate or expression of a single VEGF 120 isoform results in impaired vascular growth (H. P. Gerber et al., 1999, Development 126, 1149-1159; and P. Carmeliet et al., 1999, Nat. Med. 5, 495-502). In the adult, VEGF affects vascular growth during reproduction, wound healing, and malignant and inflammatory disorders (N. Ferrara et al., 1999, Curr. Top. Microbiol. Immunol. 237, 1-30). VEGF is currently being tested for therapeutic angiogenesis in the ischemic heart and limb, but initial clinical trials have resulted in both promising and disappointing results (J. M. Isner et al., 1999, J. Clin. Invest. 103, 1231-1236). An outstanding question is whether VEGF is able to stimulate the maturation of vessels with a smooth muscle coat (arteriogenesis). Naked endothelial channels remain vulnerable to traumatic insults, regress during changes in oxygen, and lack vasomotor control to accommodate changes in tissue perfusion (L. E. Benjamin et al., 1998, Development 125, 1591-1598). In some diseases such as pulmonary hypertension, excess arteriogenesis is an undesired and poorly controllable phenomenon. In pulmonary hypertension, remodeling of the pulmonary vasculature occurs because vascular smooth muscle cells proliferate and migrate distally around the terminal arterioles, increasing thereby the pulmonary vascular resistance. Another aspect of VEGF is that this molecule affects the permeability and growth of adult quiescent vessels. In normal human serum, no detectable levels of VEGF are present, but under pathological conditions, such as cancer and inflammatory disorders, VEGF is highly up-regulated and mediates the formation of undesired edema. Edema formation is also an important clinical problem associated with several tumors leading to ascites in peritoneal tumors, pleuritis in lung cancer and cerebral edema in brain tumors (possibly leading to fatal intracranial hypertension) and often facilitates metastasis of tumors. Vascular congestion and edema are important pathogenic mechanisms in asthma, brain infarct expansion after stroke, peritoneal sclerosis after dialysis or abdominal interventions, etc. Other VEGF homologues have been identified, but their role in angiogenesis and arteriogenesis remains unclear.

One interesting homologue of VEGF is Placental Growth Factor (PlGF) but its role in vascular growth and pathogenesis has been poorly studied (M. G. Persico et al., 1999, Curr. Top. Microbiol. Immunol. 237, 31-40). U.S. Pat. No. 5,919,899 describes PlGF and its use in the treatment of inflammatory disorders, wounds and ulcers. Donnini et al. (J. Pathol. 189, 66, 1999) have observed a correlation between up-regulation of PlGF and human meningiomas but it is clear that there is no indication whatsoever that PlGF has a role in tumor formation. The role of PlGF in edema was studied by Monsky et al. (Cancer Res. 59, 4129, 1999), but no in vivo role for PlGF in edema formation during pathological processes could be found in several mouse and human tumors.

Inhibitors for PlGF are not known in the art except for a goat polyclonal antibody against human PlGF (R&D Pharmaceuticals, Abingdon, UK) and a chicken polyclonal antibody (Gassmann et al., 1990, Faseb J. 4, 2528). Those antibodies are used for western blotting, histochemistry and immunoprecipitation studies. The role of the PlGF receptor (=VEGFR-1) for endothelial cell biology has also remained enigmatic (A. Sawano et al., 1996, Cell Growth Differ. 7, 213-221 and M. Clauss et al., 1996, J. Biol. Chem. 271, 17629-17634). Gene-targeting studies yielded conflicting results on the role of VEGFR-1, either as a possible signaling receptor (suggested by the vascular defects in VEGFR-1-deficient embryos (G. H. Fong et al., 1999, Development 126, 3015-3025)) or as an inert binding site, a "sink," for VEGF, regulating availability of VEGF for the angiogenic VEGFR-2 (suggested by the normal vascular development in mice expressing a truncated VEGFR-1, lacking the tyrosine kinase domain (S. Hiratsuka et al., 1998, Proc. Natl. Acad. Sci. U.S.A. 95, 9349-9354)).

The present invention relates to the surprising finding that PlGF is a specific modulator of VEGF during a variety of pathological conditions, such as ischemic retinopathy, tumorigenesis, inflammatory disorders, wound healing, edema and pulmonary hypertension. This finding has implications for the inhibition of vascular leakage (edema formation), inflammatory disorders, tumor formation, pathological angiogenesis and the prevention of pulmonary hypertension that occurs during pathological arteriogenesis.

DISCLOSURE OF THE INVENTION

The present invention aims at providing research tools and therapeutics for patients suffering from pathological angiogenesis, pathological arteriogenesis and edema formation. In particular, the invention aims at providing molecules, such as antibodies, small molecules, tetrameric peptides, ribozymes, antisense nucleic acids, receptor antagonists or soluble receptors that can block the activity and/or synthesis of PlGF or antagonize the VEGFR-1 activity or can inhibit the signal transduction from the VEGFR-1 to VEGFR-2. The invention further aims at using these molecules for the treatment and/or the prevention of, but not limited to, pulmonary hypertension, cancer, edema, ischemic retinopathy and inflammatory disorders. The present invention also aims at providing a method to screen for molecules that bind on VEGFR-1 or PlGF.

In other words, the present invention aims at providing therapeutics or a medicament that can be used for the treatment of pulmonary hypertension, tumor formation, edema, ischemic retinopathy or inflammatory disorders.

BRIEF DESCRIPTION OF THE DRAWING

Panel A: PlGF—constitutively produced by adult quiescent endothelial cells (EC)— is not essential for maintenance of the adult quiescent vasculature, presumably because it is ineffective in the presence of minimal VEGF expression. When expression of VEGF is up-regulated during ischemia, inflammation (macrophages: Mφ) or malignancy (tumor cells), PlGF amplifies the response of endothelial and smooth muscle cells (SMC) to VEGF, resulting in enhanced angiogenesis, vascular permeability and arteriogenesis. PlGF can act in an autocrine manner on endothelial, smooth muscle and inflammatory cells, but is also produced by nearby tumor cells, ischemic cardiomyocytes, etc. Panel B: In the absence of PlGF, vessels are normally formed during development, but respond less to VEGF during pathological conditions.

DETAILED DESCRIPTION OF THE INVENTION

Figure 1:
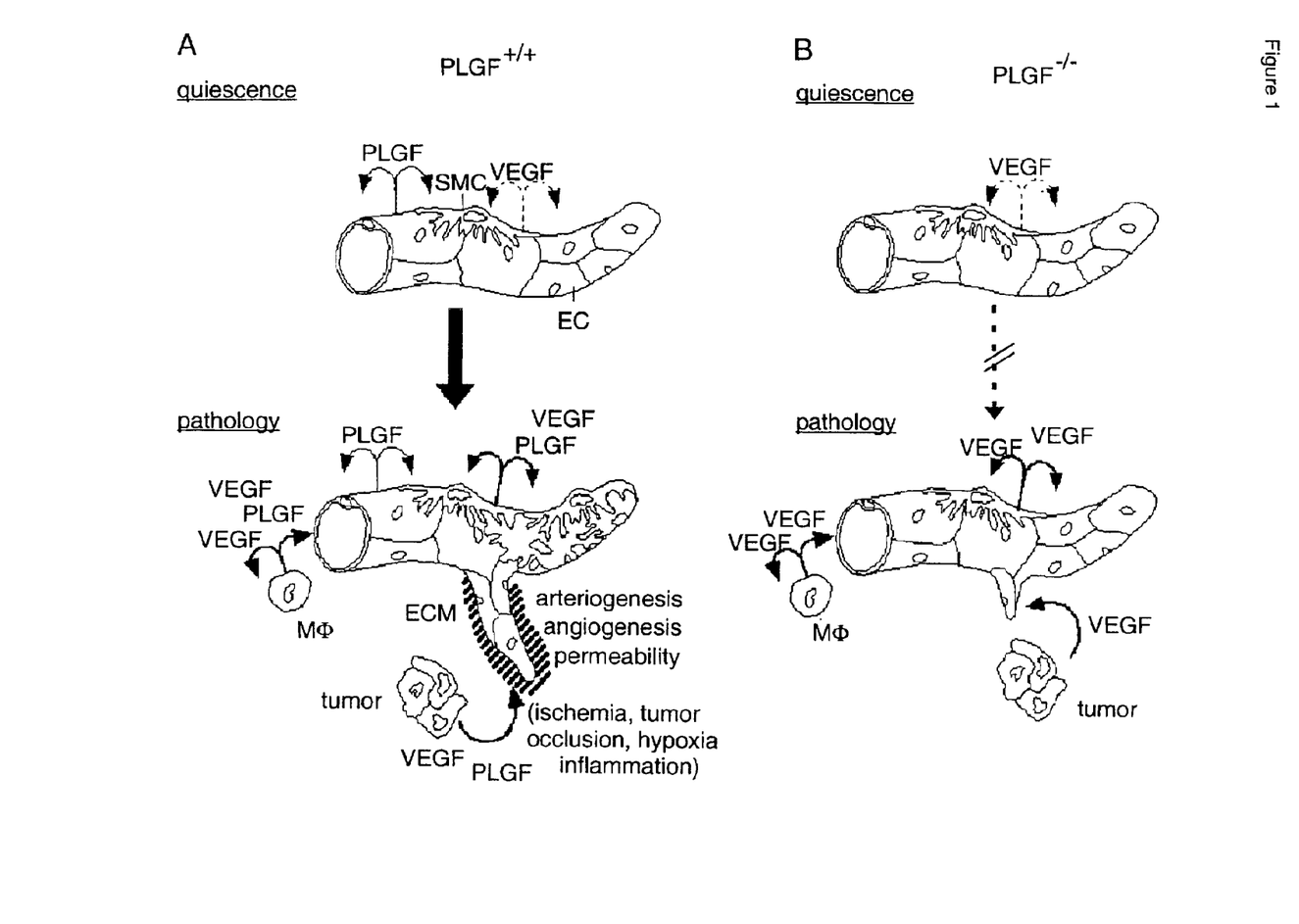
FIG. 1: Role of PlGF in pathological vascular growth.

In previous studies, the PlGF gene was inactivated in the mouse genome via homologous recombination in embryonic stem (ES) cells (P. Carmeliet, 2000, J. Pathol. 190, 387-405; P. Carmeliet, 1999, Curr. Interv. Cardiol. Reports 1, 322-335; and P. Carmeliet and D. Collen, 1999, Curr. Top. Microbiol. Immunol. 237, 133-158). PlGF-deficient (PlGF$^{-/-}$) mice are viable and fertile, and did not exhibit spontaneous vascular defects. In the present invention, it is shown that growth of endothelial channels (angiogenesis), vascular maturation by smooth muscle cells (arteriogenesis) and vascular permeability are significantly impaired in adult PlGF$^{-/-}$ mice during a variety of conditions where pathological angiogenesis and edema formation occurs. The latter conditions comprise ischemic retinopathy, tumor formation, pulmonary hypertension, edema and inflammation also known to involve VEGF. In another aspect of the invention, it is shown that the role of PlGF is not only restricted to the formation of immature capillaries, but also includes the maturation/stabilization of newly formed vessels via stimulating their coverage with smooth muscle cells (arteriogenesis), a therapeutic prerequisite for functional and sustainable angiogenesis, but an undesired effect of pathological arteriogenesis as in the case of pulmonary hypertension.

Thus, in one embodiment, the present invention relates to molecules that comprise a region that can specifically bind to placental growth factor or to vascular endothelial growth factor receptor-1; these molecules can suppress or prevent placental growth factor-induced pathological angiogenesis, vascular leakage (edema), pulmonary hypertension, tumor formation and/or inflammatory disorders. With "suppression," it is understood that suppression can occur for at least 20%, 30%, 40%, 50%, 60%, 70%, 80%, 90% or even 100%. More specifically, the invention relates to molecules that can be used to neutralize the activity of PlGF by interfering with its synthesis, translation, dimerization, receptor-binding and/or receptor-binding-mediated signal transduction.

By "molecules," it is meant peptides, tetrameric peptides, proteins, organic molecules, mutants of the VEGFR-1, soluble receptors of VEGFR-1 and any fragment or homologue thereof having the same neutralizing effect as stated above. Also, the invention is directed to antagonists of PlGF such as anti-PlGF antibodies and functional fragments derived thereof, antisense RNA and DNA molecules and ribozymes that function to inhibit the translation of PlGF, all capable of interfering/or inhibiting the VEGFR-1 signal transduction.

By "synthesis," it is meant transcription of PlGF. Small molecules can bind on the promoter region of PlGF and inhibit binding of a transcription factor or the molecules can bind the transcription factor and inhibit binding to the PlGF promoter.

By "PlGF" is also meant its isoforms, which occur as a result of alternative splicing, and allelic variants thereof. As a result of alternative splicing, three PlGF RNAs encoding monomeric human PlGF-1, PlGF-2 and PlGF-3 isoform precursors containing 149, 179 and 219 amino acid residues, respectively, have been described. In normal mouse tissues, only one mouse PlGF mRNA encoding the equivalent of human PlGF-2 has been identified.

In a specific embodiment, the invention provides a murine monoclonal antibody against PlGF. In another specific embodiment, the murine monoclonal antibody is MabPL5D11. This monoclonal antibody is available in the Department of Transgene Technology and Gene Therapy, UZ Gasthuisberg, Herestraat 49, B-3000 Leuven.

The terms "antibody" or "antibodies" relate to an antibody characterized as being specifically directed against PlGF or VEGFR-1 or any functional derivative thereof, with the antibodies being preferably monoclonal antibodies, or an antigen-binding fragment thereof, of the F(ab')$_2$, F(ab) or single chain Fv type, or any type of recombinant antibody derived thereof. These antibodies of the invention, including specific polyclonal antisera prepared against PlGF or VEGFR-1 or any functional derivative thereof, have no cross-reactivity to other proteins. The monoclonal antibodies of the invention can, for instance, be produced by any hybridoma liable to be formed according to classical methods from splenic cells of an animal, particularly of a mouse or rat immunized against PlGF or VEGFR-1 or any functional derivative thereof, and of cells of a myeloma cell line, and to be selected by the ability of the hybridoma to produce the monoclonal antibodies recognizing PlGF or VEGFR-1 or any functional derivative thereof that have been initially used for the immunization of the animals.

The monoclonal antibodies according to this embodiment of the invention may be humanized versions of the mouse monoclonal antibodies made by means of recombinant DNA technology, departing from the mouse and/or human genomic DNA sequences coding for H and L chains or from cDNA clones coding for H and L chains.

Alternatively, the monoclonal antibodies according to this embodiment of the invention may be human monoclonal antibodies. Such human monoclonal antibodies are prepared, for instance, by means of human peripheral blood lymphocytes (PBL) repopulation of severe combined immune deficiency (SLID) mice as described in PCT/EP 99/03605 or by using transgenic non-human animals capable of producing human antibodies as described in U.S. Pat. No. 5,545,806. Also, fragments derived from these monoclonal antibodies such as Fab, F(ab)'2 and ssFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies involved in the invention can be labeled by an appropriate label of the enzymatic, fluorescent, or radioactive type.

Small molecules, e.g., small organic molecules, and other drug candidates can be obtained, for example, from combinatorial and natural product libraries. To screen for the candidate/test molecules, cell lines that express VEGFR-1 and VEGFR-2 may be used and the signal transduction is monitored as described in detail in the examples.

Monitoring can be measured using standard biochemical techniques. Other responses, such as activation or suppression of catalytic activity, phosphorylation (e.g., the tyrosine phosphorylation of the intracellular domain of VEGFR-2) or dephosphorylation of other proteins, activation or modulation of second messenger production, changes in cellular ion levels, association, dissociation or translocation of signaling molecules, or transcription or translation of specific genes, may also be monitored. These assays may be performed using conventional techniques developed for these purposes in the course of screening. Inhibition of ligand binding to its cellular receptor may, via signal transduction pathways, affect a variety of cellular processes.

Cellular processes under the control of the VEGFR-1/PlGF signaling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Random peptide libraries, such as tetrameric peptide libraries further described herein, consisting of all possible combinations of amino acids attached to a solid phase support, may be used to identify peptides that are able to bind to the ligand binding site of a given receptor or other functional domains of a receptor such as kinase domains (K. S. Lam et al., 1991, Nature 354, 82). The screening of peptide libraries may have therapeutic value in the discovery of pharmaceutical agents that act to inhibit the biological activity of receptors through their interactions with the given receptor.

Identification of molecules that are able to bind to the VEGFR-1 or PlGF may be accomplished by screening a peptide library with recombinant soluble VEGFR-1 protein or PlGF protein. For example, the kinase and extracellular ligand binding domains of VEGFR-1 may be separately expressed and used to screen peptide libraries. In addition to using soluble VEGFR-1 molecules, in another embodiment, it is possible to detect peptides that bind to cell surface receptors using intact cells. The cells used in this technique may be either alive or fixed cells. The cells will be incubated with the random peptide library and will bind certain peptides in the library to form a "rosette" between the target cells and the relevant solid phase support/peptide. The rosette can thereafter be isolated by differential centrifugation or removed physically under a dissecting microscope.

In another embodiment, transdominant-negative mutant forms of VEGF receptors (e.g., a transdominant-negative receptor of VEGFR-1) can be used to inhibit the signal transduction of PlGF. The use of the transdominant-negative mutant forms of VEGF receptors is fully described in U.S. Pat. No. 5,851,999.

Also within the scope of the invention are oligoribonucleotide sequences that include antisense RNA and DNA molecules and ribozymes that function to inhibit the translation of VEGFR-1 mRNA or PlGF mRNA. Antisense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the VEGFR-1 or PlGF nucleotide sequence, are preferred. Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of VEGFR-1 or PlGF RNA sequences.

Specific ribozyme cleavage sites within any potential RNA target are initially identified by scanning the target molecule for ribozyme cleavage sites that include the following sequences, GUA, GUU and GUC. Once identified, short RNA sequences of between 15 and 20 ribonucleotides corresponding to the region of the target gene containing the cleavage site may be evaluated for predicted structural features such as secondary structures that may render the oligonucleotide sequence unsuitable. The suitability of candidate targets may also be evaluated by testing their accessibility to hybridization with complementary oligonucleotides, using ribonuclease protection assays.

Both antisense RNA and DNA molecules and ribozymes of the invention may be prepared by any method known in the art for the synthesis of RNA molecules. These include techniques for chemically synthesizing oligodeoxyribonucleotides well known in the art, such as, for example, solid phase phosphoramidite chemical synthesis.

Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be stably introduced into cell lines.

In another embodiment of the invention, the above-described molecules can be used as a medicament to treat pathological conditions of angiogenesis and/or arteriogenesis and/or edema formation.

"Edema" is a condition that is caused by vascular leakage. Vasodilation and increased permeability during inflammation can be predominant pathogenetic mechanisms. For instance, edema contributes to infarct expansion after stroke and may cause life-threatening intracranial hypertension in cancer patients. Further, extravasation of plasma proteins favors metastatic spread of occult tumors, and airway congestion may cause fatal asthmatic attacks. The increased vascular leakage that occurs during inflammation can lead to respiratory distress, ascites, peritoneal sclerosis (in dialysis patients), adhesion formation (abdominal surgery) and metastatic spreading.

By "angiogenesis," it is meant a fundamental process by which new blood vessels are formed. The primary angiogenic period in humans takes place during the first three months of embryonic development, but angiogenesis also occurs as a normal physiological process during periods of tissue growth, such as an increase in muscle or fat and during the menstrual cycle and pregnancy. The term "pathological angiogenesis" refers to the formation and growth of blood vessels during the maintenance and the progression of several disease states, for example, in blood vessels (atherosclerosis, hemangioma, hemangioendothelioma), bone and joints (rheumatoid arthritis, synovitis, bone and cartilage destruction, osteomyelitis, pannus growth, osteophyte formation, neoplasms and metastasis), skin (warts, pyogenic granulomas, hair growth, Kaposi's sarcoma, scar keloids, allergic edema, neoplasms), liver, kidney, lung, ear and other epithelia (inflammatory and infectious processes (including hepatitis, glomerulonephritis, pneumonia), asthma, nasal polyps, otitis, transplantation, liver regeneration, neoplasms and metastasis), uterus, ovary and placenta (dysfunctional uterine bleeding (due to intrauterine contraceptive devices), follicular cyst formation, ovarian hyperstimulation syndrome, endometriosis, neoplasms), brain, nerves and eye (retinopathy of prematurity, diabetic retinopathy, choroidal and other intraocular disorders, leukomalacia, neoplasms and metastasis), heart and skeletal muscle due to work overload, adipose tissue (obesity), endocrine organs (thyroiditis, thyroid enlargement, pancreas transplantation), hematopoiesis (AIDS (Kaposi), hematologic malignancies (leukemias, etc.), lymph vessels (tumor metastasis, lymphoproliferative disorders).

By "retinal ischemic diseases," it is meant that the retina's supply of blood and oxygen is decreased, and the peripheral portions of the retina lose their source of nutrition and stop functioning properly. Common diseases that lead to retinopathy are diabetic retinopathy, central retinal vein occlusion, stenosis of the carotid artery, and sickle cell retinopathy. Diabetic retinopathy is a major cause of visual loss in diabetic patients. In the ischemic retina, the growth of new blood vessels occurs (neovascularization). These vessels often grow on the surface of the retina, at the optic nerve, or in the front of the eye on the iris. The new vessels cannot replace the flow of necessary nutrients and, instead, can cause many problems such as vitreous hemorrhage, retinal detachment, and uncontrolled glaucoma. These problems occur because new vessels are fragile and are prone to bleed. If caught in its early stages, proliferative diabetic retinopathy can sometimes be arrested with panretinal photocoagulation. However, in some cases, vitrectomy surgery is the only option.

By the term "pulmonary hypertension," it is meant a disorder in which the blood pressure in the pulmonary arteries is abnormally high. In the absence of other diseases of the heart or lungs, it is called primary pulmonary hypertension. Diffuse narrowing of the pulmonary arterioles occurs as a result of pathological arteriogenesis followed by pulmonary hypertension as a response to the increased resistance to blood flow. The incidence is eight out of 100,000 people. However, pulmonary hypertension can also occur as a complication of Chronic Obstructive Pulmonary Diseases (COPD) such as emphysema, chronic bronchitis or diffuse interstitial fibrosis and in patients with asthmatiform COPD. The incidence of COPD is approximately five out of 10,000 people.

In another embodiment of the invention, the above-described molecules can be used to manufacture a medicament to treat inflammation and, more specifically, inflammatory disorders. "Inflammation," as used herein, means the local reaction to injury of living tissues, especially the local reaction of the small blood vessels, their contents, and their associated structures. The passage of blood constituents through the vessel walls into the tissues is the hallmark of inflammation, and the tissue collection so formed is termed the "exudates" or "edema." Any noxious process that damages living tissue (infection with bacteria, excessive heat, cold, mechanical injury such as crushing, acids, alkalis, irradiation, or infection with viruses) can cause inflammation irrespective of the organ or tissue involved. It should be clear that diseases of animals and man classed as "inflammatory diseases" and tissue reactions ranging from burns to pneumonia, leprosy, tuberculosis, and rheumatoid arthritis are all "inflammations."

In another embodiment of the invention, the above-described molecules can be used to manufacture a medicament to treat tumor formation. By "tumor," it is meant a mass of abnormal tissue that arises without obvious cause from pre-existing body cells, has no purposeful function, and is characterized by a tendency to autonomous and unrestrained growth. Tumors are quite different from inflammatory or other swellings because the cells in tumors are abnormal in their appearance and other characteristics. Abnormal cells, the kind that generally make up tumors, differ from normal cells in that they have undergone one or more of the following alterations: (1) hypertrophy, or an increase in the size of individual cells; this feature is occasionally encountered in tumors but occurs commonly in other conditions; (2) hyperplasia or an increase in the number of cells within a given zone; in some instances, it may constitute the only criterion of tumor formation; (3) anaplasia, or a regression of the physical characteristics of a cell toward a more primitive or undifferentiated type; this is an almost constant feature of malignant tumors, though it occurs in other instances both in health and in disease. In some instances, the cells of a tumor are normal in appearance, faithful reproductions of their parent types; the differences between them and normal body cells are difficult to discern. Such tumors are also often benign.

Other tumors are composed of cells that appear different from normal adult types in size, shape, and structure; they usually belong to tumors that are malignant. Such cells may be bizarre in form or be arranged in a distorted manner. In more extreme cases, the cells of malignant tumors are described as primitive, or undifferentiated, because they have lost the appearance and functions of the particular type of (normal) specialized cell that was their predecessor. As a rule, the less differentiated a malignant tumor's cells are, the more quickly that tumor may grow. Malignancy refers to the ability of a tumor to ultimately cause death. Any tumor, either benign or malignant in type, may produce death by local effects if it is "appropriately" situated.

The common and more specific definition of malignancy implies an inherent tendency of the tumor's cells to metastasize (invade the body widely and become disseminated by subtle means) and eventually to kill the patient unless all the malignant cells can be eradicated. Metastasis is thus the outstanding characteristic of malignancy. Metastasis is the tendency of tumor cells to be carried from their site of origin by way of the circulatory system and other channels, which may eventually establish these cells in almost every tissue and organ of the body. In contrast, the cells of a benign tumor invariably remain in contact with each other in one solid mass centered on the site of origin. Because of the physical continuity of benign tumor cells, they may be removed completely by surgery if the location is suitable. But the dissemination of malignant cells, each one individually possessing (through cell division) the ability to give rise to new masses of cells (new tumors) in new and distant sites, precludes complete eradication by a single surgical procedure in all but the earliest period of growth. A benign tumor may undergo malignant transformation, but the cause of such change is unknown. It is also possible for a malignant tumor to remain quiescent, mimicking a benign one clinically, for a long time. All benign tumors tend to remain localized at the site of origin. Many benign tumors are encapsulated. The capsule consists of connective tissue derived from the structures immediately surrounding the tumor.

Well-encapsulated tumors are not anchored to their surrounding tissues. These benign tumors enlarge by accretion, pushing aside the adjacent tissues without involving them intimately. Among the major types of benign tumors are the following: lipomas, which are composed of fat cells; angiomas, which are composed of blood or lymphatic vessels; osteomas, which arise from bone; chondromas, which arise from cartilage; and adenomas, which arise from glands. For malignant tumors, examples comprise carcinomas (occur in epithelial tissues, which cover the body (the skin) and line the inner cavitary structures of organs (such as the breast, the respiratory and gastrointestinal tracts), the endocrine glands, and the genitourinary system) and sarcomas that develop in connective tissues, including fibrous tissues, adipose (fat) tissues, muscle, blood vessels, bone, and cartilage. A cancer can also develop in both epithelial and connective tissue and is called a carcinosarcoma. Cancers of the blood-forming tissues (such as leukemias and lymphomas), tumors of nerve tissues (including the brain), and melanoma (a cancer of the pigmented skin cells) are classified separately.

In a specific embodiment, it should be clear that the therapeutic method of the present invention against tumors can also be used in combination with any other tumor therapy known in the art such as irradiation, chemotherapy or surgery.

The term "medicament to treat" relates to a composition comprising molecules as described above and a pharmaceutically acceptable carrier or excipient (both terms can be used interchangeably) to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers.

The "medicament" may be administered by any suitable method within the knowledge of the skilled man. The preferred route of administration is parenterally. In parental administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the protein, polypeptide, or peptide of the present invention is given at a dose between 1 µg/kg and 10 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 µg/kg/minute, more preferably between 7 and 15 µg/kg/minute.

In another embodiment, antibodies or functional fragments thereof can be used for the manufacture of a medicament for the treatment of the above-mentioned disorders. Non-limiting examples are the commercially available goat polyclonal antibody from R&D Pharmaceuticals, Abingdon, UK, or the chicken polyclonal antibody (Gassmann et al., 1990, Faseb J. 4, 2528). Preferentially, the antibodies are humanized (Rader et al., 2000, J. Biol. Chem. 275, 13668) and, more preferentially, human antibodies are used as a medicament.

Another aspect of administration for treatment is the use of gene therapy to deliver the above-mentioned antisense gene or functional parts of the PlGF gene or a ribozyme directed against the PlGF mRNA or a functional part thereof. "Gene therapy" means the treatment by the delivery of therapeutic nucleic acids to a patient's cells. This is extensively reviewed in Lever and Goodfellow 1995; Br. Med. Bull. 51, 1-242; Culver 1995; F. D. Ledley, 1995, Hum. Gene Ther. 6, 1129. To achieve gene therapy, there must be a method of delivering genes to the patient's cells and additional methods to ensure the effective production of any therapeutic genes. There are two general approaches to achieve gene delivery; these are non-viral delivery and virus-mediated gene delivery.

In another embodiment of the invention, a molecule to inhibit the activity of PlGF, as described above, can be used in combination with a molecule to inhibit the activity of VEGF, according to the same inhibition levels as described above for PlGF. Indeed, PlGF is found to be angiogenic at sites where VEGF levels are increased.

In another embodiment, the invention provides a method to identify molecules that can interfere with the binding of PlGF to the VEGF Receptor-1 (VEGFR-1). This method comprises exposing PlGF or VEGFR-1 to at least one molecule and measuring the ability of at least one molecule to interfere with the binding of PlGF to VEGFR-1 and monitoring the ability of at least one molecule to prevent or to inhibit pathological angiogenesis, vascular leakage, pulmonary hypertension, tumor formation and/or inflammatory disorders.

In another embodiment, the invention provides a method to identify molecules comprising: exposing placental growth factor or vascular endothelial growth factor receptor-1 and/or neuropilin-1 or nucleic acids encoding the growth factor to at least one molecule whose ability to suppress or prevent placental growth factor-induced pathological angiogenesis, vascular leakage (edema), pulmonary hypertension, tumor formation and/or inflammatory disorders is sought to be determined, and monitoring the pathological angiogenesis, vascular leakage (edema), pulmonary hypertension, tumor formation and/or inflammatory disorders.

The invention also provides methods for identifying compounds or molecules that bind on the VEGFR-1 or on PlGF and prevent the interaction between PlGF and VEGFR-1 and consequently are able to antagonize the signal transduction. The latter methods are also referred to as "drug screening assays" or "bioassays" and typically include the step of screening a candidate/test compound or agent for the ability to interact with VEGFR-1 or PlGF. Candidate compounds or agents that have this ability can be used as drugs to combat or prevent pathological conditions of angiogenesis, arteriogenesis or edema formation. Candidate/test compounds, such as small molecules, e.g., small organic molecules, and other drug candidates can be obtained, for example, from combinatorial and natural product libraries as described above.

Typically, the assays are cell-free assays, which include the steps of combining VEGFR-1 or PlGF and a candidate/test compound, e.g., under conditions that allow for interaction of (e.g., binding of) the candidate/test compound with VEGFR-1 or PlGF to form a complex, and detecting the formation of a complex in which the ability of the candidate compound to interact with VEGFR-1 or PlGF is indicated by the presence of the candidate compound in the complex. Formation of complexes between the VEGFR-1 or PlGF and the candidate compound can be quantitated, for example, using standard immunoassays. The VEGFR-1 or PlGF employed in such a test may be free in solution, affixed to a solid support, born on a cell surface, or located intracellularly.

To perform the above-described drug screening assays, it is feasible to immobilize VEGFR-1 or PlGF or its (their) target molecule(s) to facilitate separation of complexes from uncomplexed forms of one or both of the proteins, as well as to accommodate automation of the assay. Interaction (e.g., binding of) of VEGFR-1 or PlGF to a target molecule can be accomplished in any vessel suitable for containing the reactants.

Examples of such vessels include microtiter plates, test tubes, and microcentrifuge tubes. In one embodiment, a fusion protein can be provided that adds a domain that allows the protein to be bound to a matrix. For example, VEGFR-1-His or PlGF tagged can be adsorbed onto Ni-NTA microtiter plates, or VEGFR-1-ProtA or PlGF fusions adsorbed to IgG, which are then combined with the cell lysates (e.g., $^{35}$S-labeled) and the candidate compound, and the mixture incubated under conditions conducive to complex formation (e.g., at physiological conditions for salt and pH). Following incubation, the plates are washed to remove any unbound label, and the matrix immobilized and radiolabel determined directly, or in the supernatant after the complexes are dissociated. Alternatively, the complexes can be dissociated from the matrix and separated by SDS-PAGE, and the level of VEGFR-1 or PlGF binding protein found in the bead fraction quantitated from the gel using standard electrophoretic techniques. Other techniques for immobilizing protein on matrices can also be used in the drug screening assays of the invention. For example, either VEGFR-1 or PlGF and VEGFR-1 or its target molecules can be immobilized utilizing conjugation of biotin and streptavidin. Biotinylated VEGFR-1 or PlGF can be prepared from biotin-NHS (N-hydroxy-succinimide) using techniques well known in the art (e.g., biotinylation kit, Pierce Chemicals, Rockford, Ill.) and immobilized in the wells of streptavidin-coated 96-well plates (Pierce Chemical). Alternatively, antibodies reactive with VEGFR-1 or PlGF, but which do not interfere with binding of the protein to its target molecule, can be derivatized to the wells of the plate, and VEGFR-1 or PlGF trapped in the wells by antibody conjugation. As described above, preparations of a VEGFR-1-binding protein or PlGF and a candidate compound are incubated in the VEGFR-1 or PlGF-presenting wells of the plate, and the amount of complex trapped in each well can be quantitated.

Methods for detecting such complexes, in addition to those described above for the GST-immobilized complexes, include immunodetection of complexes using antibodies reactive with the VEGFR-1-target molecule or PlGF, or reactive with VEGFR-1 or PlGF and compete with the target molecule, as well as enzyme-linked assays that rely on detecting an enzymatic activity associated with the target molecule. Another technique for drug screening that provides for high throughput screening of compounds having suitable binding affinity to VEGFR-1 or PlGF is described in detail in "Determination of Amino Acid Sequence Antigenicity" by H. N. Geysen, WO 84/03564, published on Sep. 13, 1984. In summary, large numbers of different small peptide test compounds are synthesized on a solid substrate, such as plastic pins or some other surface. The protein test compounds are reacted with fragments of VEGFR-1 or PlGF and washed. Bound VEGFR-1 or PlGF is then detected by methods well known in the art. Purified VEGFR-1 or PlGF can also be coated directly onto plates for use in the aforementioned drug screening techniques. Alternatively, non-neutralizing antibodies can be used to capture the peptide and immobilize it on a solid support. This invention also contemplates the use of competitive drug screening assays in which neutralizing antibodies capable of binding VEGFR-1 or PlGF specifically compete with a test compound for binding VEGFR-1 or PlGF. In this manner, the antibodies can be used to detect the presence of any protein, which shares one or more antigenic determinants with VEGFR-1 or PlGF.

In another embodiment, the invention provides a method for the production of a pharmaceutical composition comprising the usage of the method according to claims 6-7 and further mixing the molecule identified, or a derivative or homologue thereof, with a pharmaceutically acceptable carrier.

In another embodiment, PlGF promoter polymorphisms can be used to identify individuals having a predisposition to acquire pathological angiogenesis, vascular leakage (edema), pulmonary hypertension, tumor formation and/or inflammatory disorders. Indeed, it can be expected that promoter polymorphisms can give rise to much higher or much lower levels of PlGF. Consequently, higher levels of PlGF can lead to a predisposition to acquire pathological angiogenesis, vascular leakage (edema), pulmonary hypertension, tumor formation and/or inflammatory disorders while much lower levels of PlGF can lead to a protection to acquire pathological angiogenesis, vascular leakage (edema), pulmonary hypertension, tumor formation and/or inflammatory disorders.

The following examples more fully illustrate preferred features of the invention, but are not intended to limit the invention in any way. All of the starting materials and reagents disclosed below are known to those skilled in the art, and are available commercially or can be prepared using well-known techniques.

EXAMPLES

1. Impaired Pathological Angiogenesis in PlGF$^{-/-}$ Mice

In several pathological conditions, in particular when associated with increased VEGF expression, formation of new endothelial-lined channels (angiogenesis) was significantly impaired in PlGF$^{-/-}$ mice. Growth and angiogenesis of embryonic stem (ES) cell-derived tumors, known to be mediated by VEGF (N. Ferrara et al., 1996, Nature 380, 439-442), was also dependent on PlGF. Indeed, PlGF$^{+/+}$ ES cell-derived tumors obtained within four weeks after subcutaneous inoculation in nu/nu PlGF$^{+/+}$ mice, weighed 4±1 g (n=8) and appeared hemorrhagic and bled profusely (seven of eight tumors). In contrast, PlGF$^{-/-}$ tumors in nu/nu PlGF$^{-/-}$ hosts only weighed 1.0±0.3 g (n=8) and were homogeneously white with minimal bleeding (five of seven tumors). Growth and vascularization in PlGF$^{-/-}$ tumors were reduced to the same degree as in VEGF$^{-/-}$ tumors. PlGF$^{+/+}$ and PlGF$^{-/-}$ tumors contained comparable vascular densities of endothelial cords and capillaries (diameter <8 µm). However, compared to PlGF$^{+/+}$ tumors PlGF$^{-/-}$ tumors contained fewer medium-sized or large vessels. In a previous study, we demonstrated that formation of medium-sized and large vessels is dependent on VEGF (P. Carmeliet et al., 1998, Nature 394, 485-490). Angiogenesis of PIGF$^{+/+}$ tumors in nu/nu PIGF$^{-/-}$ mice or of PIGF$^{-/-}$ tumors in nu/nu PIGF$^{+/+}$ mice was comparable to that of PIGF$^{+/+}$ tumors in nu/nu PIGF$^{+/+}$ mice, indicating that production of PIGF, either by tumor or by host-derived tissue, could rescue the phenotype. VEGF transcript levels were comparable between both genotypes (VEGF/$10^3$ HPRT mRNA molecules: 280±20 in PIGF$^{+/+}$ tumors versus 320±50 in PIGF$^{-/-}$ tumors; p=NS) and were expressed in epithelial and mesenchymal cells throughout PIGF$^{+/+}$ tumors, whereas PIGF was expressed in endothelial cells of small and large vessels (in situ hybridization). Expression of VEGF-B and VEGF-C was also comparable.

Exposure of neonatal mice to 80% oxygen from P7 to P12 causes capillary dropout in the retina due to reduced VEGF expression (VEGF/$10^3$ HPRT mRNA molecules in PIGF$^{+/+}$ retinas: 270±40 at P7 during normoxia versus 100±10 at P12 during hyperoxia; p<0.05 versus P7; n=5) (T. Alon et al., 1995, Nat. Med. 1, 1024-1028). Upon reexposure to room air at P12, retinal ischemia up-regulates VEGF expression (VEGF/$10^3$ HPRT mRNA molecules: 390±50 at P13, p<0.05 versus P7; and 165±50 at P17; n=5), thereby inducing venous dilatation, arterial tortuosity, and capillary outgrowth in the vitreous chamber by P17 (T. S. Kern et al., 1996, Arch. Opthalmol. 114, 986-990). The role of PIGF in ischemic retinopathy remains unknown. PLGF transcript levels (PIGF/$10^3$ HPRT mRNA molecules) were 40±10 at P7 (normoxia), 10±2 at P12 (hyperoxia), 90±10 at P13 (return to normoxia) and 12±2 at P17. Despite a comparable retinal vascular development during normoxia and a comparable capillary dropout during hyperoxia (P12) in both genotypes, PIGF$^{+/+}$ mice developed ~75% fewer and significantly smaller neovascular vitreous tufts by P17 than PIGF$^{+/+}$ mice (endothelial cells per section: 10±2 in PIGF$^{-/-}$ mice versus 48±4 in PIGF$^{+/+}$ mice; n=6; p<0.05). In addition, PIGF$^{-/-}$ mice exhibited reduced venous dilatation (semiquantitative dilatation score, see methods: 0.9±0.05 in PIGF$^{-/-}$ mice versus 1.7±0.03 in PIGF$^{+/+}$ mice; p<0.05) and arterial tortuosity (tortuosity score: 0.8±0.05 in PIGF$^{-/-}$ mice versus 2.3±0.2 in PIGF$^{+/+}$ mice; p<0.05).

2. Reduced Vascular Permeability in PIGF$^{-/-}$ Mice

Vascular permeability, a characteristic feature of VEGF (N. Ferrara et al., 1999, Curr. Top. Microbiol. Immunol. 237, 1-30), was consistently reduced in PIGF$^{-/-}$ mice as compared to PIGF$^{+/+}$ mice. VEGF has been previously implicated in vascular permeability of the skin (L. F. Brown et al., 1995, J. Immunol. 154, 2801-2807), but the role of PIGF remains undetermined. Several models were used: (i) Intradermal injection of 1, 3 or 10 ng VEGF$_{165}$ induced less extravasation of Evans blue in PIGF$^{-/-}$ mice than in PIGF$^{+/+}$ mice (Miles assay). (ii) Skin sensitization with ovalbumin caused less extravasation of plasma in PIGF$^{-/-}$ mice than in PIGF$^{+/+}$ mice (J. Casals-Stenzel et al., 1987, Immunopharmacology 13, 177-183) (Arthus reaction: 12±1 µl extravasated plasma after vehicle versus 130±5 µl plasma after ovalbumin in PIGF$^{+/+}$ mice; p<0.05; n=12 as compared to 11±1 µl plasma after vehicle versus 13±1 µl plasma after ovalbumin in PIGF$^{-/-}$ mice; p=NS; n=12). (iii) Plasma extravasation in normal skin vessels was similar in both genotypes (mg plasma×$10^5$/min. mg tissue: 35±5 in PIGF$^{+/+}$ mice versus 35±4 in PIGF$^{-/-}$ mice; p=NS; n=7) but increased significantly more in PIGF$^{+/+}$ than in PIGF$^{-/-}$ mice after skin wounding (60±4 in PIGF$^{+/+}$ mice versus 40±4 in PIGF$^{-/-}$ mice; p<0.05; n=10). Thus, PIGF specifically increased the vascular permeability in response to VEGF, but not to histamine.

3. Impaired Pathological Arteriogenesis in PIGF$^{-/-}$ Mice

Healing of skin wounds is mediated by ingrowth of vessels, which initially consist of endothelial cells (angiogenesis) and subsequently become surrounded by smooth muscle cells (arteriogenesis). VEGF has been implicated in capillary growth during skin healing (M. Detmar et al., 1998, J. Invest. Dermatol. 111, 1-6), but the role of PIGF remains unknown. Healing of skin incisions was slightly retarded in PIGF$^{-/-}$ as compared to PIGF$^{+/+}$ mice. Both genotypes contained comparable densities of thrombomodulin-stained vessels in unwounded skin (vessels/mm$^2$: 240±80 in PIGF$^{+/+}$ mice versus 200±80 in PIGF$^{-/-}$ mice; p=NS; n=5). Smooth muscle α-actin staining revealed a comparable density of vessels (i) that were not covered or surrounded by a few smooth muscle cells (vessels/mm$^2$: 58±14 in PLGF$^{+/+}$ mice versus 40±12 in PIGF$^{-/-}$ mice; p=NS; n=5), and (ii) that were completely covered by at least one smooth muscle cell layer (vessels/mm$^2$: 15±5 in PIGF$^{+/+}$ mice versus 19±1 in PIGF$^{-/-}$ mice; p=NS; n=5). Within four days after wounding, PIGF was expressed in endothelial cells, and PIGF and VEGF were up-regulated in PIGF$^{+/+}$ keratinocytes in the hyperplastic epidermis at the wound edge, where new vessels formed (in situ hybridization; not shown). Both strains contained comparable vessel ingrowth in the wound region (thrombomodulin-stained vessels/mm$^2$: 240±50 in PIGF$^{+/+}$ mice versus 180±50 in PIGF$^{-/-}$ mice; n=5; p=NS). However, both genotypes differed in the degree the new vessels were covered by SMA-positive smooth muscle cells. The number of vessels that were not or incompletely covered by smooth muscle cells was 40±7 in PIGF$^{+/+}$ mice versus 84±13 in PIGF$^{-/-}$ mice (p<0.05; n=5), whereas the number of vessels that were completely covered by at least one smooth muscle cell layer was 75±18 in PIGF$^{+/+}$ mice versus 30±10 in PIGF$^{-/-}$ mice (p<0.05). Thus, lack of PIGF impairs coverage of new endothelial channels with smooth muscle cells.

Pulmonary hypertension due to hypoxia-induced remodeling of the pulmonary vasculature is a life-threatening complication of chronic obstructive pulmonary disease (COPD). Even though VEGF is highly up-regulated in lungs of patients with COPD (C. D. Cool et al., 1999, Am. J. Pathol. 155, 411-419) and of hypoxic animals (H. Christou et al., 1998, Am. J. Respir. Cell. Mol. Biol. 18, 768-776), its role in this process is not understood. Surprisingly, no information is available about the expression or role of PIGF. Therefore, adult mice were exposed to hypoxia (10% $O_2$) during four weeks, as this causes pulmonary hypertension due to increased "muscularization" of the pulmonary vessels (C. A. Hales et al., 1983, Am. Rev. Respir. Dis. 128, 747-751). The ratio of the right ventricular (RV) to left ventricular (LV) weight (a measure of RV hypertrophy) was comparable in both genotypes during normoxia (32±2% in PIGF$^{+/+}$ mice versus 33±2% in PIGF$^{-/-}$ mice; n=4; p=NS), significantly increased after hypoxia in PIGF$^{+/+}$ mice (48±4%; n=5; p<0.05 versus normoxia), but only minimally affected by hypoxia in PIGF$^{-/-}$ mice (37±2%; n=6; p<0.05 versus normoxia and versus PIGF$^{+/+}$). Significant genotypic differences in pulmonary vascular remodeling were observed. Elastin staining of normoxic lungs revealed that both genotypes had a comparable density of intra-acinar thin-walled arterioles containing only an internal elastic lamina (IEL), or thick-walled arterioles containing an intact IEL plus an incomplete external elastic lamina (EEL) (Table 1). Thick-walled arterioles containing two intact elastic laminae over their entire circumference were only occasionally detected in both genotypes (Table 1). Hypoxia caused significant vascular remodeling in PIGF$^{+/+}$ mice, resulting in a larger fraction of thick-walled vessels with a partial or complete EEL at the expense of thin-walled vessels with only a single IEL (Table 1). In contrast, vascular remodeling was much less significant in PIGF$^{-/-}$ mice, resulting in a smaller fraction of thick-walled vessels with a complete IEL and EEL (Table 1). Immunostaining for smooth muscle α-actin (SMA) confirmed that PIGF$^{+/+}$ mice contained significantly more fully muscularized arterioles than PIGF$^{-/-}$ mice after hypoxia (Table 1). Protection against pulmonary hypertension in PIGF$^{-/-}$ mice was not due to a reduced vasoconstriction response (RV pressure increased by 31±4% in PIGF$^{+/+}$ mice versus 34±5% in PIGF$^{-/-}$ mice in response to 30 minutes 7% $O_2$; p=NS), nor was it due to lower hematocrit levels (48±3% in PIGF$^{+/+}$ mice versus 53±3% in PIGF$^{-/-}$ mice; p=NS). Thus, PIGF significantly modulates arterial remodeling.

TABLE 1

Pulmonary vascular remodelling after chronic hypoxia.

| | Vessels per $10^3$ alveoli | | | |
|---|---|---|---|---|
| | PLGF$^{+/+}$ mice | | PLGF$^{-/-}$ mice | |
| | 20% $O_2$ | 10% $O_2$ | 20% $O_2$ | 10% $O_2$ |
| Presence of elastic laminae | | | | |
| Single IEL | 11 ± 2 | 3.6 ± 0.6* | 11 ± 1 | 5.6 ± 0.6*, # |
| IEL + incomplete EEL | 11 ± 2 | 12 ± 1 | 10 ± 2 | 11 ± 1 |
| IEL + complete EEL | <0.5 | 6 ± 1* | <0.5 | 3 ± 1*, # |
| Coverage by SMC | | | | |
| Absent | 2.4 ± 0.9 | 0.5 ± 0.3* | 3.1 ± 0.7 | 3.4 ± 0.7* |
| Incomplete | 11 ± 1 | 12 ± 2 | 8 ± 2 | 11 ± 1 |
| Complete | 1.2 ± 0.5 | 11 ± 2*, # | 2.6 ± 2 | 2.8 ± 2*, # |

The data represent the number (average±SEM in five mice) of vessels per $10^3$ alveoli containing a single internal elastic lamina (IEL), an IEL plus an incomplete external elastic lamina (EEL), or an IEL plus a complete EEL. In addition, the density of vessels that were not (absent), incompletely or completely surrounded by smooth muscle α-actin stained smooth muscle cells (SMC) is shown. *: p<0.05 versus normoxia (20% $O_2$); #: p<0.05 versus PLGF$^{+/+}$.

4. Synergism Between PlGF and VEGF

Proliferation and survival of endothelial cells in response to VEGF were studied. VEGF$_{165}$ stimulated proliferation of PIGF$^{+/+}$ endothelial cells (Table 2) and protected them against apoptosis induced by serum deprivation (0.1% serum) or supplementation of TNF-α (10 ng/ml). In contrast, VEGF$_{165}$ failed to stimulate proliferation or to protect PIGF$^{-/-}$ endothelial cells against serum deprivation- or TNF-α-induced apoptosis (Table 2). PIGF itself was not mitogenic nor anti-apoptotic for endothelial cells of either genotype. Also, it did not affect the response of PIGF$^{+/+}$ endothelial cells to VEGF (Table 2), likely because PIGF$^{+/+}$ endothelial cells already produced sufficient PIGF (the variable degree of PLGF production by endothelial cells and the relative amounts of VEGF present in the culture conditions may in fact explain why some, but not others, have previously observed an angiogenic response in vitro). However, PIGF rescued the impaired proliferation and survival response of PIGF$^{-/-}$ endothelial cells to VEGF$_{165}$ (Table 2). PIGF was also found to modulate the mitogenic response to VEGF of smooth muscle cells, known to express VEGFR-1 and VEGFR-2 (C. L. Grosskreutz et al., 1999, Microvasc. Res. 58, 128-136). Indeed, VEGF stimulated proliferation of PIGF$^{+/+}$ but not of PIGF$^{-/-}$ smooth muscle cells. PIGF, ineffective by itself, restored the responsiveness of PIGF$^{-/-}$ cells to VEGF. PIGF specifically modulated the activity of VEGF, since PIGF$^{-/-}$ and PIGF$^{+/+}$ cells displayed comparable responses to bFGF. Thus, PIGF affected endothelial and smooth muscle cells only when they were stimulated with VEGF.

The mechanism found to play a role in the synergism between VEGF and PlGF: (i) PlGF up-regulated the expression of VEGF, as previously suggested (M. J. Bottomley et al., 2000, Clin. Exp. Immunol. 119, 182-188). Expression of VEGF by PIGF$^{-/-}$ fibroblasts was increased by PlGF (VEGF production per $10^6$ cells/ml/24 hours: 180±10 pg after treatment with vehicle versus 440±10 pg after treatment with 100 ng/ml PIGF for 48 hours; p<0.05 versus vehicle). Similar results were obtained for PIGF$^{+/+}$ fibroblasts (VEGF production per $10^6$ cells/ml/24 hours: 200±8 pg after treatment with vehicle versus 430±5 pg after treatment with 100 ng/ml PIGF for 48 hours; p<0.05 versus vehicle).

Induction of VEGF production by PIGF was, however, smaller than that induced by hypoxia (1% $O_2$) (expressed per $10^6$ cells/ml/24 hours: 3200±150 pg for PIGF$^{+/+}$ cells; 2400±150 pg for PIGF$^{-/-}$ cells; p<0.05 versus normoxia). VEGF immunoreactivity was also increased in PIGF$^{+/+}$ mice after treatment with 1.5 μg PIGF$_{132}$/24 hours.

TABLE 2

Role of PLGF and VEGF in endothelial proliferation.

| | Endothelial proliferation | |
|---|---|---|
| | PLGF$^{+/+}$ | PLGF$^{-/-}$ |
| Vehicle | 11 ± 2 | 11 ± 1 |
| VEGF$^{120}$ (100 ng/ml) | 22 ± 1* | 12 ± 1 |
| VEGF$^{165}$ (100 ng/ml) | 36 ± 4* | 12 ± 2 |
| VEGF$^{165}$ (300 ng/ml) | 42 ± 3* | 13 ± 3 |
| VEGF-E (100 ng/ml) | 32 ± 1* | 13 ± 1 |
| PLGF (100 ng/ml) | 11 ± 1 | 11 ± 1 |
| VEGF$^{165}$ (100 ng/ml) + PLGF (100 ng/ml) | 33 ± 3* | 33 ± 2* |
| VEGF$^{165}$(100 ng/ml) | | |
| + anti-NP1 MoAb | 27 ± 3* | N.D. |
| + anti-NP2 MoAb | 34 ± 3 | N.D. |
| + anti-VEGFR-1 Ab | 23 ± 5* | 12 ± 2 |
| + anti-VEGFR-2 MoAb | 15 ± 2 | N.D. |
| VEGF$^{165}$ (100 ng/ml) + PLGF (100 ng/ml) | | |
| + anti-VEGFR-1 Ab | 22 ± 4 | 21 ± 4 |
| + anti-VEGFR-2 MoAb | 13 ± 3 | 17 ± 2 |
| bFGF (50 ng/ml) | 35 ± 2* | 35 ± 5* |
| bFGF (50 ng/ml) + PLGF (100 ng/ml) | 32 ± 3* | 33 ± 1* |

The data represent the mean±SD of nine to twelve experiments. *: p<0.05 versus control (vehicle). None of the antibodies affected baseline endothelial proliferation in the absence of VEGF (not shown). Ab: polyclonal antiserum; MoAb: monoclonal antibodies; bFGF: basic fibroblast growth factor.

5. PIGF Specifically Modulates the Responsiveness to VEGF

Since VEGF plays a role in the above-mentioned phenotypes of angiogenesis, arteriogenesis and permeability, we investigated whether PlGF determined the responsiveness to VEGF. Subcutaneous implantation of matrigel (A. Passaniti et al., 1992, Lab. Invest. 67, 519-528) supplemented with $VEGF_{165}$ ($VEGF_{165}$) induced a strong angiogenic response in $PlGF^{+/+}$ but not in $PlGF^{-/-}$ mice (hemoglobin content: 0.28±0.02 g/dl in $PlGF^{+/+}$ mice versus 0.02±0.02 g/dl in $PlGF^{-/-}$ mice; n=15; p<0.05).

In contrast, basic fibroblast growth factor (bFGF) induced a similar angiogenic response in both genotypes (hemoglobin content: 0.28±0.02 g/dl in $PlGF^{+/+}$ mice versus 0.25±0.02 g/dl in $PlGF^{-/-}$ mice; n=15; p=NS). These observations were confirmed by histological analysis and immunostaining for endothelial factor VIII-related antigen.

The reduced response of $PlGF^{-/-}$ endothelial cells to VEGF was confirmed using cultured primary $PlGF^{-/-}$ endothelial cells. $VEGF_{165}$ (100 ng/ml) was chemotactic for $PlGF^{+/+}$ but not for $PlGF^{-/-}$ endothelial cells, whereas both genotypes responded comparably to bFGF. PlGF (100 ng/ml) itself was not chemotactic for endothelial cells of either genotype and did not affect the response of $PlGF^{+/+}$ endothelial cells to VEGF, likely because endothelial cells already produce abundant PlGF. However, PlGF completely restored the impaired migration of $PlGF^{-/-}$ endothelial cells in response to $VEGF_{165}$. PlGF also enhanced the chemo-attractive activity of VEGF on smooth muscle cells, known to express VEGFR-1 and VEGFR-2 (C. L. Grosskreutz et al., 1999, Microvasc. Res. 58, 128-136). VEGF stimulated the migration of $PlGF^{+/+}$ but not of $PlGF^{-/-}$ smooth muscle cells, whereas bFGF stimulated smooth muscle cells of both genotypes. Similar effects were observed for SMC proliferation. Even though PlGF alone did not stimulate the cells, it rescued the impaired smooth muscle cell response to VEGF, further underscoring that PlGF is essential for the biological activity of VEGF. Thus, PlGF determines and synergistically amplifies the response to VEGF.

6. Inhibition of PlGF Impairs Pulmonary Hypertension

Wild-type mice are injected with different concentrations of a murine anti-PlGF antibody (0 µg, 1 µg, 5 µg, 10 µg and 50 µg). Murine anti-PlGF antibody is generated in the $PlGF^{-/-}$ mouse. After 72 hours, the mice are placed for four weeks in a tightly sealed chamber under normobaric hypoxia ($FiO_2$ 10%). After 28 days, the mice are sacrificed and used for histological analysis as described in the materials and methods section. The control mouse with 0 µg anti-PlGF antibody developed a serious hypoxia-induced pulmonary vascular remodeling. The murine anti-PlGF antibody prevents this pulmonary vascular remodeling at very low concentrations.

7. Inhibition of PlGF Impairs Inflammation

Occlusion of a supply artery is a frequent complication of atherosclerosis or arterial restenosis and deprives downstream tissues of oxygen and nutrients. However, coincident enlargement of preexisting collaterals due to endothelial activation and smooth muscle growth (adaptive arteriogenesis) may allow residual perfusion to the ischemic regions and prevent tissue necrosis in the territory of the occluded artery. Even though administration of VEGF protein or VEGF gene transfer has been shown to improve collateral growth, the role of endogenous VEGF remains controversial. PlGF has not been previously implicated in this process. Macrophages play a role in adaptive arteriogenesis, but the role of PlGF remains unknown. Therefore, the role of macrophages in adaptive arteriogenesis of collateral arterioles was studied after ligation of the femoral artery. Mac3-positive macrophages, known to play an essential role in collateral growth, were found to adhere to the endothelium and to infiltrate in and through the wall of the collaterals three days after ligation. However, more collaterals were infiltrated by Mac3-positive macrophages in $PlGF^{+/+}$ than in $PlGF^{-/-}$ mice (45 of 66 $PlGF^{+/+}$ collaterals versus 29 of 67 $PlGF^{-/-}$ collaterals; p<0.05 by Chi-square analysis; n=5 mice). This may relate to the known monocyte chemo-attractant activity of PlGF. Indeed, using another model of leukocyte attraction (local endotoxin injection in the footpad), three-fold more leukocytes infiltrated in $PlGF^{+/+}$ than in $PlGF^{-/-}$ vessels (CD45-positive cells/vessel: 5.2±1 in $PlGF^{+/+}$ mice versus 1.5±0.2 µm in $PlGF^{-/-}$ mice; n=5; p<0.05). Macrophages may also modulate collateral growth via production of PlGF (8±2 $PlGF/10^3$ HPRT mRNA molecules; n=5). Another characteristic feature of adaptive arteriogenesis is the extravasation of fibronectin, providing a scaffold for migrating smooth muscle cells. Extravasation of fibronectin was greater in $PlGF^{+/+}$ than in $PlGF^{-/-}$ collaterals, as revealed by the more numerous collateral vessels, surrounded by fibronectin-immunoreactive deposits (57 of 80 $PlGF^{+/+}$ collaterals versus 21 of 83 $PlGF^{-/-}$ collaterals; n=5 mice; p<0.05 by Chi-Square). The increased permeability in $PlGF^{+/+}$ collaterals may be caused by the synergism between PlGF and VEGF, known to be released by activated macrophages. VEGF levels in thioglycolate-stimulated peritoneal macrophages were 200±11 $VEGF/10^3$ HPRT mRNA molecules (n=5). Thus, PlGF is essential for collateral growth.

8. Preparation of Monoclonal Antibodies Against PlGF

Since PlGF deficiency reduces the phenotype of diverse pathological processes of angiogenesis, arteriogenesis and vascular leakage comprising ischemic retinopathy, tumor formation, pulmonary hypertension, vascular leakage (edema formation) and inflammatory disorders, molecules that can inhibit the formation of PlGF, or binding PlGF to its receptor (VEGFR-1), or signal transduction initiated by PlGF, can be useful to treat the above-mentioned pathological processes. Monoclonal antibodies against murine PlGF-2 were produced essentially as previously described (P. J. Declerck et al. (1995) J. of Biol. Chem. 270, 8397), however, using mice with inactivated PlGF genes. The mice were immunized by subcutaneous injection of murine PlGF-2 (R&D Systems). In total, 120 hybridomas were produced, of which 15 showed a 50% inhibition, 38 showed 70% inhibition and five gave complete inhibition of binding of rmPlGF-2 to its receptor (Flt-1). This was measured in an immunofunctional ELISA in which 96-well plates were coated with 100 µl of 1 µg/ml of rmFlt-1/Fc chimera overnight at room temperature in PBS. After blocking for one hour with 1% BSA in PBS, 100 µl of a mixture of 70 µl of hybridoma medium pre-incubated with 70 µl of recombinant mPlGF-2 at 10 ng/ml for two hours at room temperature was applied to the plate. A standard of rmPlGF-2 ranging from 20 ng/ml to 156 pg/ml was included (diluted in PBS-Tween.BSA-EDTA). Plates were incubated one hour at 37° C. and one hour at room temperature, washed five times with PBS-Tween and 100 µl of biotinylated goat anti-murine PlGF-2 at 200 ng/ml was applied for two hours at room temperature. After washing five times with PBS-Tween, 100 µl of avidin-HRP conjugate (Vectastorin ABC kit) was applied for one hour at room temperature. After washing five times with PBS-Tween, the plate was developed with 90 μl of o-phenylene diamine in citrate phosphate buffer, pH 5.0, for 30 minutes and measured at 490 nm.

The five positive clones (PL1H5, PL5D11, PL9F7, PL13F11, PL17A10) were subcloned, grown and injected in mice (PIGF knockouts in Balb/c background) to produce ascites. The monoclonal antibodies were purified on protein-A Sepharose and again tested for inhibition of binding of m-PIGF-2 to Flt-1/Fc. The results (Table 3) indicate that Mab-PL5D11 markedly inhibits binding of m-PIGF-2 to its receptor. This Mab was selected for evaluation in the edema model (mustard oil skin application).

TABLE 3

Inhibition by anti-murine PIGF-2 Mab of murine PIGF-2 binding to murine Flt-1/Fc. The data represent residual m-PIGF-2 in percent.

| Nr | | Molar excess versus m-PIGF-2 | | | | |
|---|---|---|---|---|---|---|
| | | 10× | 5× | 2.5× | 1.25× | No antibody |
| 1 | PL1H5G5 | 66 | 64 | 63 | 89 | 100 |
| 2 | PL5D11D4 | 10 | 15 | 22 | 43 | 100 |
| | PL5D11F10 | 14 | 19 | 22 | 35 | 100 |
| 3 | PL13F11C8 | 57 | 70 | 83 | 100 | 100 |
| 4 | PL17A10E12 | 40 | 46 | 60 | 89 | 100 |
| | PL17A10F12 | 41 | 41 | 53 | 90 | 100 |
| Negative control | Irrelevant antibody 1 C 8 | 100 | 100 | 100 | 100 | 100 |
| Concentration of m-PIGF-2 in ng/ml | | 5 | 5 | 5 | 5 | 5 |
| Concentration of antibody in ng/ml | | 200 | 100 | 50 | 25 | 0 |

9. Validation of the PIGF Monoclonals in a Mustard Oil Skin Application Model Mustard oil was painted on the ears of Swiss mice, and extravasation of Evans blue was determined. Antibodies were injected intravenously at 300 μg/kg 30 minutes before injection of Evans blue and application of mustard oil. Briefly, 100 μl of a test agent was injected via a jugular vein catheter, followed 30 minutes later by an intravenous injection of 300 μl of 0.5% Evans blue. One ear was painted with 0.1% mustard oil and repainted again 15 minutes later. After 30 minutes, the mouse was perfused via the left ventricle with saline containing 100 U/ml heparin, followed by 3% paraformaldehyde in citrate buffer. The ears were amputated, dissected in small segments and extracted overnight in formamide at 55° C. The absorbance of the extraction fluid was measured at 610 nm.

Anti-PIGF antibodies, which blocked the PIGF response of endothelial cells (Table 4), reduced vascular leakage in wild-type mice application of mustard oil on their ears (relative absorbance units/ear: 13±3 after mineral oil; 53±7 after mustard oil plus control IgGs; 26±5 after mustard oil plus anti-PIGF; n=5; p<0.05).

TABLE 4

Effect of mustard oil on Evans blue extravasation.

| Group | | $A^{610}$ nm | p |
|---|---|---|---|
| No antibody | | 0.76 ± 0.09 | — |
| PL5D11D4 | 10 μg | 0.50 ± 0.05 | 0.12 |
| PL17A10E12 | 10 μg | 0.37 ± 0.04 | 0.03 |

10. Isolation of PIGF Inhibitors by Screening of a Tetrameric Library

A tetrameric library has been assayed for its ability to inhibit in ELISA assays the binding between the recombinant mouse Placental Growth Factor 2 (mPIGF-2) (R&D Systems Cat. No. 645-PL) and the recombinant mouse Vascular Endothelial Growth Factor Receptor 1 (VEGF R1) Flt-1/Fc chimera (R&D Systems, Cat. No. 471-F1). The ELISA assay was performed following this procedure. The receptor was coated on a microtiter plate (Costar, Cat. No. 3590) at 1 μg/ml in $NaH_2PO_4$ 50 mM, NaCl 150 mM pH 7.5 (PBS), 100 μl/well, for 16 hours at room temperature. The wells were washed five times with PBS containing 0.004% Tween (PBS-T) and blocked with Bovine Serum Albumin (BSA) 1% in PBS, 150 μl/well, for two hours at room temperature. The plate was washed with PBS-T five times, and 100 μl of mPIGF diluted at 8 ng/ml in PBS pH 7.5, BSA 0.1%, EDTA 5 mM, Tween 0.004% (PBET), was added to each well. After the incubation for one hour at 37° C. and one hour at room temperature, the plate was washed again, and biotinylated anti-mPIGF antibodies (R&D Systems, Cat. No. BAF 465) were added at 200 ng/ml in PBET, 100 μl/well, and incubated for two hours at room temperature. The plate was washed five times with PBS-T, 100 μl/well of a solution containing an avidin-biotin system (Vectastatin Elite ABC kit, Vector Laboratories, Cat. No. PK 6100). This solution was prepared by mixing one drop of solution A and one drop of solution B in 2.5 ml of Tris-HCl 50 mM and diluting this mix 1/100 in PBET. After one hour of incubation, the plate was washed as above, and 90 μl/well of a solution containing 1 mg/ml of O-Phenylenediamine (OPD) in citrate buffer pH 5.0 was added to each well. After 40 minutes, the developing reaction was stopped by adding 30 μl/well of sulfuric acid 3M. The plate was read at 490 nm with an ELISA reader. To test the inhibitory activity of the library, each pool of the library was added in competition with mPIGF using a molar excess of 1000 times (1:1000, 1:2000 means a molar excess of 2000; 1:1500 means a molar excess of 1500, etc.). The results of the screening are shown in Table 5.

TABLE 5

| | | plate 1 OD 490 nm |
|---|---|---|
| mPIGF 8 ng/ml | 100 | 0.993 |
| mPIGF 5 ng/ml | 67.673716 | 0.672 |
| R&D mAb (1:5) | 51.0574018 | 0.507 |
| 1 D-Ala | 80.5639476 | 0.8 |
| 2 D-Asp | 75.5287009 | 0.75 |
| 3 D-Val | 80.5639476 | 0.8 |
| 4 D-Glu | 57.4018127 | 0.57 |
| 5 L-Cha | 87.6132931 | 0.87 |
| 6 D-Phe | 79.0533736 | 0.785 |
| 7 D-Thr | 83.5850957 | 0.83 |
| 8 D-Met | 84.592145 | 0.84 |
| 9 D-Cys(Acm) | 91.6414904 | 0.91 |
| 10 D-Lys | 88.8217523 | 0.882 |
| 11 D-Tyr | 90.6344411 | 0.9 |
| 12 D-Pro | 93.6555891 | 0.93 |
| 13 D-Leu | 95.367573 | 0.947 |
| 14 D-His | 107.75428 | 1.07 |
| 15 D-Gln | 101.711984 | 1.01 |
| 16 D-Trp | 101.711984 | 1.01 |
| 17 D-Arg | 105.740181 | 1.05 |
| 18 D-Asn | 106.747231 | 1.06 |
| 19 D-Ile | 103.222558 | 1.025 |
| 20 D-Arg(Tos) | 103.323263 | 1.026 |

TABLE 5-continued

|  | plate 2 | OD 490 nm |
|---|---|---|
| mPIGF 8 ng/ml | 100 | 0.991 |
| mPIGF 5 ng/ml | 71.6448032 | 0.71 |
| 21 D-Ser | 83.6528759 | 0.829 |
| 22 L-Cys(Acm) | 83.8546922 | 0.831 |
| 23 L-Cys(Bzl) | 84.7628658 | 0.84 |
| 24 L-Cys(p-MeBzl) | 89.3037336 | 0.885 |
| 25 L-Cys(tBu) | 92.0282543 | 0.912 |
| 26 L-Mt(O) | 83.9556004 | 0.832 |
| 27 L-Met(O2) | 78.6074672 | 0.779 |
| 28 L-Glu(a-Oall) | 92.244898 | 0.904 |
| 29 b-Ala | 100 | 0.98 |
| 30 Gly | 92.1428571 | 0.903 |
| 4 D-Glu 1:500 | 86.1884368 | 0.805 |
| 4 D-Glu 1:1000 | 59.1006424 | 0.552 |
| 4 D-Glu 1:1500 | 48.2869379 | 0.451 |
| 4 D-Glu 1:2000 | 39.9357602 | 0.373 |
| 2 D-Asp 1:500 | 89.9357602 | 0.84 |
| 2 D-Asp 1:1000 | 78.9079229 | 0.737 |
| 2 D-Asp 1:1500 | 78.0513919 | 0.729 |
| 2 D-Asp 1:2000 | 74.9464668 | 0.7 |
| 14 D-His 1:500 | 96.6809422 | 0.903 |
| 14 D-His 1:1000 | 101.391863 | 0.947 |
| 14 D-His 1:1500 | 100.535332 | 0.939 |
| 14 D-His 1:2000 | 96.8950749 | 0.905 |

Thirty pools of 900 different tetrameric peptides were screened for the possibility to interfere with the binding of mPIGF-2 to mVEGFR-1. Clearly, pool 4 on Table 5 (with D-Glu on the terminal position) has inhibitory activity when compared with two anti-PIGF antibodies to interfere with binding (R&D mAb and a homemade mAb) of mPIGF-2 to mVEGFR-1.

Materials and Methods

Models of Angiogenesis

Morphometric analysis of myocardial, renal, and retinal angiogenesis in neonatal mice was performed as described (P. Carmeliet et al., 1999, Nat. Med. 5, 495-502).

Matrigel assay: Ingrowth of capillaries in matrigel was performed as described (A. Passaniti et al., 1992, Lab. Invest. 67, 519-528). Briefly, 500 μl ice-cold matrigel containing heparin (300 μg/ml) and VEGF (100 ng/ml), or basic fibroblast growth factor (bFGF; 100 ng/ml) was injected subcutaneously. After seven days, the matrigel pellet with the neovessels was dissected for analysis of neovascularization: one part was homogenized to determine the hemoglobin content determined using Drabkin's reagent (Sigma, St. Quentin Fallavier, France), whereas the other part was fixed in 1% paraformaldehyde for histological analysis.

ES-tumor model: For ES cell-derived tumor formation, $5 \times 10^6$ ES cells were subcutaneously injected into PIGF$^{+/+}$ Nu/Nu or PIGF$^{-/-}$ Nu/Nu mice, obtained by intercrossing PIGF$^{+/+}$ Nu/Nu mice, as described (P. Carmeliet et al., 1998, Nature 394, 485-490). Vascular densities were quantitated by counting the number of endothelial cords and capillaries (diameter <8 μm), medium-sized vessels (diameter 10-25 μm), or large vessels (diameter >30 μm) per field (1.2 mm$^2$) in six to eight randomly chosen optical fields on three to five adjacent sections (320 μm apart) per tumor using the Quantimet Q600 imaging system.

Ischemic retina model: Retinal ischemia was induced by placing P7 neonatal mice in a cage of hyperbaric (80%) oxygen for five days, after which they were returned for another five days in normal room air, as described (L. E. Smith et al., 1994, Invest. Opthalmol. Vis. Sci. 35, 101-111). Fluorescent retinal angiography and endothelial cell counts on retinal cross-sections were determined as reported (H. P. Hammes et al., 1996, Nat. Med. 2, 529-533). Venous dilatation and arterial tortuosity were semi-quantitatively scored on a scale from 0-3.

Wound models: Vascular remodeling during skin wound healing was analyzed within four days after occurrence of a 10 mm full-thickness skin wound on the back of the mouse, as described (S. Frank et al., 1995, J. Biol. Chem. 270, 12607-12613). Wound healing was scored by daily measurements of the width of the wound.

Pulmonary hypertension: Adult mice were placed for four weeks in a tightly sealed chamber under normobaric hypoxia (FiO$_2$ 10%), as described (C. A. Hales et al., 1983, Am. Rev. Respir. Dis. 128, 747-751). After 28 days, mice were used for measurements of hematocrit, using an automated cell counter (Abbott Cell-Dyn 1330 system, Abbott Park, Ill.) and for histological analysis. Right ventricular pressures (RVP) were measured in anesthetized ventilated mice (sodium pentobarbital, 60 mg/kg, i.p.) by transthoracic puncture using high-fidelity pressure micromanometers (Millar) after inhalation of a gas mixture containing 20% O$_2$ or 7% O$_2$. For histology, mice were perfused with 1% phosphate-buffered paraformaldehyde at 100 cm H$_2$O pressure via the heart and at 30 cm H$_2$O pressure through the trachea. Visualization of the internal elastic lamina (IEL) and external elastic lamina (EEL) was achieved using Hart's elastin stain. Hypoxia-induced pulmonary vascular remodeling was assessed by counting the number of non-muscularized (only IEL) and partially (IEL plus incomplete EEL) or fully (IEL plus complete EEL) muscularized peripheral vessels (landmarked to airway structures distal to the terminal bronchioli) per 100 alveoli in fields containing $5 \times 500$ alveoli (C. A. Hales et al., 1983, Am. Rev. Respir. Dis. 128, 747-751).

Vascular Permeability

Arthus reaction (allergen-induced edema formation in the skin (J. Casals-Stenzel et al., 1987, Immunopharmacology 13, 177-183)): mice were sensitized by intraperitoneal (i.p.) injection of saline (1 ml/kg) containing ovalbumin (40 μg/kg; Sigma, St. Louis, Mo.) and Al(OH)$_3$ (0.2 mg/ml added to the antigen solution one hour prior to injection) on days 0 and 2.

Vascular leakage was quantified 14 days after presensitization by determining the amount of intravenously injected 125I-bovine serum albumin (BSA) and Evans blue dye accumulating in the skin injection site. Therefore, the fur on the dorsal skin of anaesthetized mice was shaved, and 1.5 μCi/kg of 125I-BSA (2.8 μCi/μg; NEN-Dupont, France) mixed with a solution of Evans blue dye in sterile saline (15 mg/kg) was injected i.v. Ten minutes later, ovalbumin (100 ng/site) was injected at four intradermal sites. After 60 minutes, the degree of vascular leakage was quantified: (i) by measuring the diameter of the edematous spot (visualized by its coloration) using a micrometer; and (ii) by determining the amount of extravasated plasma protein at each skin site (expressed as μl extravasated plasma) after normalizing the 125I-cpm in the skin (10 mm punch) for the 125I-cpm in 1 μl of plasma.

Miles assay: Vascular permeability was assayed using the Miles assay (N. McClure, 1994, J. Pharmacol. Toxicol. Methods). Briefly, mice were shaved and injected with 50 μl of a solution containing 0.5% Evans blue in saline 45 minutes prior to intradermal injection of 20 μl phosphate-buffered saline (PBS) containing 1, 3 or 10 ng recombinant human VEGF$_{165}$; pictures were taken 45 minutes later.

Skin healing: After shaving, a standardized 15 mm full-thickness skin incision was made on the back of anesthetized mice, taking care not to damage the underlying muscle. Extravasation of 125I-BSA (expressed as g plasma/g tissue/ min) was measured as described (R. G. Tilton et al., 1999, Invest. Opthalmol. Vis. Sci. 40, 689-696).

In Vitro Angiogenesis Assays

Endothelial and smooth muscle cell culture: In order to obtain mouse capillary endothelial cells, anesthetized mice were injected s.c. with 500 μl of ice-cold matrigel containing bFGF (100 ng/ml) and heparin (100 μg/ml). After seven days, the matrigel pellet was dissected and enzymatically dispersed using 0.1% type II collagenase (Sigma, St. Louis, Mo.). Mouse endothelial cells were routinely cultured in T75 flasks coated with 0.1% gelatin in M131 medium supplemented with 5% MVGS (Gibco-BRL). Smooth muscle cells from mouse aorta were harvested and cultured as described (J. M. Herbert et al., 1997, FEBS Lett. 413, 401-404). Before stimulation, cells were starved in medium with 0.5% serum for 24 hours, after which they were stimulated with human $VEGF_{165}$ and/or murine PlGF, or bFGF (all from R&D, Abingdon, UK) for 24 hours before analysis of the total cell number (proliferation) or the number of cells migrated after scrape-wounding (migration).

Synthesis of a Tetrameric Library

A tetrameric library has been synthesized using commercially available 9-Fluorenylmethoxycarbonyl (Fmoc)-derivatized amino acids (purity >99%). All derivatives are listed in Table 6 along with catalog numbers and company names (provider) from which they have been purchased.

TABLE 6

List of building blocks used throughout the peptide library preparation.

| Number | Building block 3-letter code | Building block | Protected derivative | Provider | Catalog number |
|---|---|---|---|---|---|
| 1 | D-Ala | D-Alanine | Nα-Fmoc-D-Alanine | Chem-Impex Intl | 02372 |
| 2 | D-Asp | D-Aspartic acid | Nα-Fmoc-D-Aspartic acid (t-butyl ester) | Chem-Impex Intl | 02478 |
| 3 | D-Val | D-Valine | Nα-FmocD-Valine | Chem-Impex Intl | 02471 |
| 4 | D-Glu | D-Glutamic acid | Nα-Fmoc-D-Glutamic acid (t-butyl ester) | Chem-Impex Intl | 02479 |
| 5 | L-Cha | L-Cyclohexylalanine | Nα-Fmoc-L-Cyclohexylalanine | Sygena | FC-01-003-117 |
| 6 | D-Phe | D-Phenylalanine | Nα-Fmoc-D-Phenylalanine | Novabiochem | 04-13-1030 |
| 7 | D-Thr | D-Threonine | Nα-Fmoc-D-Threonine (O-t-butyl-ether) | Chem-Impex Intl | 02483 |
| 8 | D-Met | D-Methionine | Nα-Fmoc-D-Methionine | Novabiochem | 04-13-1003 |
| 9 | D-Cys(Acm) | D-Cysteine(S-acetamydomethyl) | Nα-Fmoc-D-Cysteine(S-acetamydomethyl) | Novabiochem | 04-13-1054 |
| 10 | D-Lys | D-Lysine | Nα-Fmoc-D-Lysine(N$^{ε}$-butyloxycarbonyl) | Alexis | 104-041-G005 |
| 11 | D-Tyr | D-Tyrosine | Nα-Fmoc-D-Tyrosine(O-t-butyl-ether) | Chem-Impex Intl | 02465 |
| 12 | D-Pro | D-Proline | Nα-Fmoc-D-Proline | Novabiochem | 04-13-1031 |
| 13 | D-Leu | D-Leucine | Nα-Fmoc-D-Leucine | Chem-Impex Intl | 02427 |
| 14 | D-His | D-Histidine | Nα-Fmoc-D-Histidine(N$^r$-trytil) | Alexis | 104-034-G005 |
| 15 | D-Gln | D-Glutamine | Nα-Fmoc-D-Glutamine (N-trytil) | Novabiochem | 04-13-1056 |
| 16 | D-Trp | D-Triptophan | Nα-Fmoc-D-Triptophan(N$^{in}$-t-butyloxycarbonyl) | Chem-Impex Intl | 02484 |
| 17 | D-Arg | D-Arginine | Nα-Fmoc-D-Arginine(N$^r$-pentamethylchroman) | Alexis | 104-113-G005 |
| 18 | D-Asn | D-Asparagine | Nα-Fmoc-D-Asparaqine (N-trytil) | Chem-Impex Intl | 02477 |
| 19 | D-Ile | D-Isoleucine | Nα-Fmoc-D-Isoleucine | Chem-Impex Intl | 03448 |
| 20 | D-Arg(Tos) | D-Arginine(N$^r$-Tosyl) | Nα-Fmoc-D-Arginine(N$^r$-Tosyl) | Chem-Impex Intl | 02382 |
| 21 | D-Ser | D-serine | Nα-Fmoc-D-serine(O-t-butyl-ether) | Alexis | 104-066-G005 |
| 22 | L-Cys(Acm) | L-Cysteine(S-acetamydomethyl) | Nα-Fmoc-L-Cysteine(S-acetamydomethyl) | Chem-Impex Intl | 02396 |
| 23 | L-Cys(Bzl) | L-Cysteine(S-benzyl) | Nα-Fmoc-L-Cysteine(S-benzyl) | Novabiochem | 04-12-1015 |
| 24 | L-Cys(p-MeBzl) | L-Cysteine(S-p-methyl-benzyl) | Nα-Fmoc-L-Cysteine(S-p-methoxy-benzyl) | Chem-Impex Intl | 02399 |

TABLE 6-continued

List of building blocks used throughout the peptide library preparation.

| Number | Building block 3-letter code | Building block | Protected derivative | Provider | Catalog number |
|---|---|---|---|---|---|
| 25 | L-Cys(tBu) | L-Cysteine(S-tert-butyl) | Nα-Fmoc-L-Cysteine(S-tert-butyl) | Novabiochem | 04-12-1016 |
| 26 | L-Met(O) | L-Methionine-sulphone | Nα-Fmoc-L-Methionine-sulphone | Novabiochem | 04-12-1112 |
| 27 | L-Met(O)$_2$ | L-Methionine-sulphoxide | Nα-Fmoc-L-Methionine-sulphoxide | Novabiochem | 04-12-1113 |
| 28 | L-Glu(β-OAll) | L-Glutamic acid-(β-allyl) | Nα-Fmoc-L-Glutamic acid-(β-allyl) | Novabiochem | 04-12-1158 |
| 29 | β-Ala | β-Alanine | Nα-Fmoc-β-Alanine | Chem-Impex Intl | 02374 |
| 30 | Gly | Glycine | Nα-Fmoc-Glycine | Chem-Impex Intl | 02416 |

The library has been built onto the following scaffold (G. Fassina et al. (1996) *J. Mol. Recogn.* 9, 564; M. Marino et al. *Nat. Biotechn.* (1997) 18, 735):

where G represents the amino acid Glycine and K represents the amino acid L-Lysine onto which three levels of randomization have been achieved by applying the Portioning-Mixing method (A. Furka et al. (1991) *Int. J. Pept. Protein. Res.* 37, 487; K. S. Lam (1991) *Nature* 354, 82). The total number of peptides generated ($N_t$) can be calculated by the following formula:

$$N_t = B^x$$

Where B is the number of building blocks used (30) and x is the number of randomization (3).

a) Synthesis of the Scaffold

The initial scaffold has been prepared by manual solid phase synthesis starting from 419 mg of Fmoc-Gly-derivatized 4-hydroxymethylphenoxyacetic polystyrene resins (PS-HMP) (substitution 0.75 mmol/g, Novabiochem Cat. No. 04-12-2053), corresponding to 314 μmol of Glycine onto which two subsequent couplings with Fmoc-L-Lys(Fmoc)-OH (Chem-Impex Intl. Cat. No. 01578) have been carried out. The resin has been placed in a 35 ml polypropylene cartridge endowed with a polypropylene septum (AllTech, Cat. No. 210425) and washed three times with 4.0 ml of N,N-dimethylformamide (DMF, Peptide synthesis grade, LabScan, Cat. No. H6533). To remove the Fmoc protection, the resin has been treated for 15 minutes with 5.0 ml of 20% Piperidine (BIOSOLVE LTD, Cat. No. 16183301) in DMF and then washed three times with 4.0 ml of DMF. For the coupling of the first Lysine, 1.5 mmol of Fmoc-L-Lys(Fmoc)-OH (0.87 g) have been dissolved in 6.0 ml of DMF and then activated by adding 3.0 ml of a 0.5 M solution of 2-(1H-Benzotriazol-yl)-1,1,3,3-tetramethyl-uronium tetrafluoroborate (TBTU, >99%, Chem-Impex Intl, Cat. No. 02056) and 1-Hydroxybenzotriazole (HOBt, SIGMA-ALDRICH, Cat. No. H2006) in DMF and 3.0 ml of a 1 M solution of Di-isopropyl-ethylamine (DIEA, SIGMA-ALDRICH, Cat. No. D-3387) in DMF. After four minutes stirring at room temperature, the solution has been transferred onto the resin and stirred for 30 minutes. To remove the excess of amino acid, the resin has been washed three times with 4.0 ml of DMF. The deprotection of the Lysine-Fmoc groups has been achieved by treating the resin for 15 minutes with 5.0 ml of 20% Piperidine in DMF and washing three times with 4.0 ml of DMF to remove the excess of reagent. For the coupling of the second Lysine, 3.0 mmol of Fmoc-L-Lys(Fmoc)-OH (1.77 g) have been dissolved in 6.0 ml of DMF and then activated adding 6.0 ml of a 0.5 M solution of TBTU/HOBt in DMF and 6.0 ml of DIEA in DMF. After four minutes stirring at room temperature, the solution has been transferred onto the resin and stirred for 30 minutes. The resin has then been washed three times with 4.0 ml of DMF. The final Fmoc groups have been removed by treatment with 10.0 ml of 20% Piperidine in DMF for 15 minutes. The resin has then been submitted to the following washings:

| Solvent | Number of washes | Volume (ml) |
|---|---|---|
| DMF | 3 | 4.0 |
| MeOH* | 3 | 4.0 |
| Et$_2$O** | 3 | 4.0 |

*Methanol (MeOH, LabScan, Cat. No. A3513)
**Ethyl Ether (Et$_2$O, LabScan, Cat. No. A3509E)

The resin has been dried by applying a Nitrogen stream and then weighed. The final weight of the resin was 442 mg.

b) Assembly of the Library

The library has been generated by applying the following procedure:

b.1 Resin Splitting into 30 Equal Aliquots.

The resin has been transferred into a 50 ml polypropylene graduated tube and 35 ml of DMF:DCM (2:3) (DCM, Dichloromethane, LabScan, Cat. No. H6508L) have been added. The suspension has been thoroughly mixed and fractions of 1.0 ml have been dispensed in 30 polypropylene syringes (3 ml) endowed with filtration septa at the bottom (Shimadzu Corp. Cat. No. 292-05250-02). The remaining volume of suspension has been diluted up to 35 ml with DMF:DCM (2:3) and 1.0 ml fractions have been again dispensed into the syringes. The graduated tube has been once again filled up to 30 ml and 1.0 ml aliquots distributed into the syringes. The syringes have been vacuum drained from the bottom and the resins washed once with 1.0 ml of DMF. The syringes, labeled with numbers from 1 to 30, contained an equal fraction of resin corresponding to around 10 μmoles of scaffold (40 μmoles of $NH_2$ groups).

b.2 Coupling of the First Random Residue (Position 3).

0.75 M stock solutions in DMF of the 30 amino acids (listed in Table 5) have been prepared and stored at 4° C. until use. To carry out couplings and deprotection on sub-libraries, from this step forward, a PSSM8 eight-channel peptide synthesizer (Shimadzu Corp.) has been used. The syringes have been placed into the synthesizer and 267 μl (200 μmoles) of amino acids have been dispensed into 2 ml polypropylene tubes (Eppendorf, Cat. No. 24299). The machine automatically performs activations, acylations, deprotections and washings. Activations were carried out using 400 μl of a 0.5 M solution in DMF of TBTU/HOBt plus 400 μl of a 1 M solution in DMF of DIEA. Acylations have been carried out for 30 minutes, mixing the suspensions by bubbling nitrogen from the bottom of the syringes. Deprotection have been carried out for 15 minutes with 0.9 ml of 20% piperidine/DMF, while washings have been performed with 0.9 ml of DMF (three times, two minutes).

In the first round, amino acids 1 to 8 have been coupled, in the second round, amino acids 9 to 16 were coupled, in the third round, amino acids 17 to 24 were coupled, and in the final round, amino acids 25 to 30 were coupled.

b.3 Mixing and Re-Splitting of Resins.

To each syringe, 500 μl of DMF:DCM (2:3) have been added and the resins suspended by gentle swirling. The suspensions have been removed from the syringes, collected in a 50 ml polypropylene tube (graduated) and thoroughly mixed by vigorous shaking.

After addition of DMF:DCM (2:3) up to a final volume of around 35 ml, 1.0 ml aliquots of suspension have been re-dispensed into the 30 syringes, repeating the operations described in step 1 ("Resin splitting into 30 equal aliquots"). At the end, the resins have been washed once with 1.0 ml of DMF.

b.4 Coupling of the Second Random Residue (Position 2).

All operations described in step 2 ("Coupling of the first random residue") were repeated.

b.5 Mixing and Re-Splitting of Resins.

All operations described in step 3 ("Mixing and re-splitting of resins") were repeated.

b.6 Coupling of the Third Known Residue (Position 1).

All operations described in step 2 ("Coupling of the first random residue") have been repeated.

b.7 Final Washes and Drying of the Resins.

The resins were washed three times with 1 ml of DCM, three times with 1 ml of MeOH, and two times with 1 ml of $Et_2O$. The resins have then been dried under vacuum.

b.8 Cleavage.

Thirty ml of a TFA-$H_2$O-TIS (100:5:5, v/v/v) mixture (TIS, tri-iso-propylsilane, SIGMA-ALDRICH Cat. No. 23, 378-1) have been freshly prepared and 800 μl added to each syringe. After vortexing for three hours, the resins have been filtered off, collecting the acidic solution directly in 15 ml polypropylene tubes (labeled with numbers from 1 to 30) containing 5 ml of cold $Et_2O$. The white precipitates have been separated by centrifugation at 3000 rpm for ten minutes and the organic solvents discarded. The precipitates have been washed once with 5 ml of cold $Et_2O$ and, after centrifugation, were dissolved in 2.0 ml of $H_2O$/$CH_3CN$/TFA 50:50:01 and lyophilized. Ten mg/ml stock solutions of the peptide libraries in DMSO have been prepared and stored in sealed vials at −80° C.

What is claimed is:

1. A method of treating pathological angiogenesis occurring during the maintenance and the progression of tumor formation in a subject in need thereof, said method comprising the step of administering, to the subject an antibody or an antigen-binding fragment thereof, wherein said antibody or antigen-binding fragment thereof comprises a region that specifically binds to placental growth factor (PlGF) and inhibits the activity of PlGF, thereby suppressing said pathological angiogenesis.

2. The method according to claim 1, wherein said antibody is a monoclonal antibody.

3. The method according to claim 1, wherein said antibody has been humanized.

4. The method according to claim 1, wherein said antibody or antigen-binding fragment thereof is a Fab, F(ab)'2, scFv fragment or a recombinant antibody.

5. A method of treating tumor growth in a subject, said method comprising the step of administering to the subject an antibody or antigen-binding fragment thereof that specifically binds placental growth factor (PlGF) thereby inhibiting PlGF activity and reducing said tumor growth.

6. The method according to claim 1, wherein said treatment is combined with other tumor therapy.

7. The method according to claim 6, wherein said other tumor therapy is selected from the group consisting of irradiation, chemotherapy, and surgery.

8. The method according to claim 5, wherein said treatment is combined with other tumor therapy.

9. The method according to claim 8, wherein said other tumor therapy is selected from the group consisting of irradiation, chemotherapy, and surgery.

* * * * *

UNITED STATES PATENT AND TRADEMARK OFFICE
CERTIFICATE OF CORRECTION

PATENT NO. : 7,482,004 B2
APPLICATION NO. : 10/291979
DATED : January 27, 2009
INVENTOR(S) : Peter Carmeliet et al.

It is certified that error appears in the above-identified patent and that said Letters Patent is hereby corrected as shown below:

On the title page:
In ITEM (75) Inventors:     change "Ruvo Menotti, Tervico (IT)" to
--Ruvo Menotti, Trevico (IT)--

In ITEM (73) Assignees:     change "Life Sciences Research Partners vzw., Leuven (BE)"
to --D. Collen Research Foundation vzw, Leuven (BE)--

In the specification:

| | | |
|---|---|---|
| COLUMN 1, | LINE 21, | change "(PlGF-)" to --(PlGF$^{-/-}$)-- |
| COLUMN 5, | LINE 6, | change "(SLID)" to --(SCID)-- |
| COLUMN 5, | LINE 10, | change "ssFv" to --scFv-- |
| COLUMN 13, | LINE 33, | change "PlGF$^{+/+}$" to --PlGF$^{-/-}$-- |
| COLUMN 13, | LINE 46, | change "ofVEGF" to --of VEGF-- |
| COLUMN 21, | LINE 54, | change "PlGF$^{+/+}$Nu/Nu" to --PlGF$^{+/-}$ *Nu/Nu*-- |
| COLUMN 26, | LINE 23, | change "D-3387)" to --D-3887)-- |

Signed and Sealed this
Twenty-fifth Day of October, 2011

David J. Kappos
*Director of the United States Patent and Trademark Office*